US006203758B1

(12) United States Patent
Marks et al.

(10) Patent No.: US 6,203,758 B1
(45) Date of Patent: Mar. 20, 2001

(54) MICRO-CIRCUIT SYSTEM WITH ARRAY OF FUNCTIONALIZED MICRO-ELECTRODES

(75) Inventors: Robert Marks, Beersheva; Jean-Paul Lellouche, Ashdod, both of (IL)

(73) Assignee: Bio-Pixel Ltd., Beer-Sheva (IL)

( * ) Notice: Subject to any disclaimer, the term of this patent is extended or adjusted under 35 U.S.C. 154(b) by 0 days.

(21) Appl. No.: 08/966,618

(22) Filed: Nov. 10, 1997

(51) Int. Cl.[7] .............................. C25C 1/14; G01N 15/06; G01N 21/64; G01N 33/543; C12Q 1/68; B01D 17/06; C07D 311/82; A61L 51/103

(52) U.S. Cl. ........................... 422/68.1; 204/22; 204/112; 204/403; 204/418; 204/419; 204/434; 422/68.1; 422/82.01; 422/82.02; 422/82.03; 422/101; 250/461.1; 250/461.2; 435/6; 435/16; 435/7.1; 435/970; 435/973; 205/687; 549/223; 436/518; 436/525; 427/2.11; 427/2.13; 427/455; 427/470

(58) Field of Search .............................. 204/112, 22, 403, 204/418, 419, 434; 422/68.1, 101, 82.01, 82.02, 82.03; 250/461.1, 461.2, 687; 435/6, 16, 5, 7.1, 970, 973; 549/223; 427/2.11, 2.13, 455, 470; 436/518, 525; 205/687

(56) References Cited

U.S. PATENT DOCUMENTS

| | | | | |
|---|---|---|---|---|
| 4,512,855 | * | 4/1985 | Mazur ................................... | 204/22 |
| 5,532,128 | * | 7/1996 | Eggers et al. ........................ | 435/16 |
| 5,605,662 | | 2/1997 | Heller ................................. | 422/68.1 |
| 5,607,646 | * | 3/1997 | Okano et al. ........................ | 422/101 |
| 5,632,957 | * | 5/1997 | Heller et al. ........................ | 422/68.1 |
| 5,641,630 | * | 6/1997 | Snitman et al. ..................... | 435/6 |
| 5,667,667 | * | 9/1997 | Southern .............................. | 205/687 |

FOREIGN PATENT DOCUMENTS

WO 95/12808   10/1994   (WO) ............................ G01N/21/00

OTHER PUBLICATIONS

Livache et al, "Preparation of a DNA Matrix Via an Electrochemically Directed Copolymerization of Pyrrole and Oligonucleotides Bearing a Pyrrole Group", *Nucleic Acids Research*, 22(15):2915–2921, (1994).

Livache et al, "Biosensing Effects on Functionalized Electroconducting Conjugated Polymer Layers: Addressable DNA Matrix for the Detection of Gene Mutations", Synthetic Metals, 71: 2143–2146 (1995).

Roget et al, "Electrochemically Directed Copolymerization of Pyrrole and Oligonucleotides", *Nucleoside & Nucleotides*, 14(3–5)L 943–946 (1995).

Noble, DF., "DNA Sequencing on a Chip", *Analytical Chemistry*, 67(5): 201–204 (1995).

Bains, W., "The Chip of the 90s", *Chemistry in Britain* Feb., 1995, pp. 122–125.

Wallraff et al, "DNA Sequencing on a Chip" *Chemtech*, Feb. 1997, pp. 22–32.

(List continued on next page.)

Primary Examiner—James C. Housel
Assistant Examiner—Gailene R. Gabel
(74) Attorney, Agent, or Firm—Mark M. Friedman

(57) ABSTRACT

A micro-circuit for performing analyses of multimolecular interactions and for performing molecular syntheses, comprising: (a) a support; (b) at least one micro-electrode attached to the support, the micro-electrode being selectively electronically activated and the micro-electrode having a protective layer which is removable; (c) a binding entity for attachment to the at least one micro-electrode, the binding entity being capable of attachment to at least one micro-electrode when the protective layer has been removed; and (d) a power source being operatively connected to at least one micro-electrode for electronically activating at least one micro-electrode. The micro-circuit of the present invention also includes embodiments featuring a micro-circuit reader for detecting the interaction of the binding entity to a complementary probe, as well as methods for making and using the micro-circuit of the present invention.

21 Claims, 19 Drawing Sheets

Step 1

OTHER PUBLICATIONS

Frank, R., "Spot Synthesis: An Easy Technique for the Positionally Addressable, Parallel Chemical Synthesis on a Membrane Support", *Tetrahedron*, 48(42): 9217–9232 (1992).

Southern et al, "Arrays of Complementary Oligonucleotides for Analysing the Hybridisation Behavior of Nucleic Acids", *Nucleic Acids Research*, 22(8): 1368–1373 (1994).

Matson et al, "Bipolymer Synthesis on Polypropylene Supports: Oligonucleotide Arrays", *Analytical Biochemistry*, 224: 110–116 (1995).

Schena et al, "Parallel Human Genome Analysis: Microarray–Based Expression Monitoring of 100 Genes", *Proc. Natl. Acad. Sci.*, 93: 10614–10619 (1996).

* cited by examiner

Step 1

Step 2

Step 3  Completed DNA Biochip Bearing the Appropriate DNA Probe Array

Oligodeoxynucleotide probes possessing a thiol group: Generic structures of type A

$n_1$, $n_2$ variable, X = $CH_2$ or NH

Oligodeoxynucleotide probes possessing a disulfide group: Generic structures of type B1

$n_1$, $n_2$ variable, X = $CH_2$ or NH

**Oligodeoxynucleotide probes possessing a disulfide group:
Generic structures of type B2 Based on Lipoic Acid**

$n_2$ variable, X = CH$_2$ or NH

Oligodeoxynucleotide probes possessing a thiol or sulfide group: Two-dimensioned hydrogen bond based surface array $n_1$ variable, X = $CH_2$ or NH α-Silylated Ethers or Dithianes as Self-Assembled Monolayer Thiol / Disulfide Precursors Incorporating Amide / Urethane Subgroups α-Silylated Ethers or Dithianes as Self-Assembled Monolayer Thiol / Disulfide Precursors Incorporating a (1,3)-Diyne Subgroup Photopolymerized Self-assembled Monolayers $R_1$, $R_2$ and $R_3$ = alkyl or aryl groups
$n_1$ and $n_2$ variable Oligodeoxynucleotide Probes Possessing an Hydroxylamine or Hydrazine Group: Generic Structures of Type C $n_1, n_2$ variable, $X_1 = CH_2$ or $O$
$R = O-NH_2$ or $NH-NH_2$ α-Silylated Ethers or Dithianes as Self-Assembled Monolayer Precursors Incorporating Amide / Urethane Subgroups: Functionalization of Indium Tin Oxide Electrodes (ITO Electrodes)

$R_1$, $R_2$, $R_3$ and $R_4$ = alkyl or aryl groups
$n_1$ and $n_2$ variable, X = Cl, Br or I New Microarray Reader
(case of ITO Electrode Arrays)

New Remote Microarray Reader
(case of ITO Electrode Arrays)

Multiplexed Remote Reader
(case of Electrode Arrays of Any Type)

MICRO-CIRCUIT SYSTEM WITH ARRAY OF FUNCTIONALIZED MICRO-ELECTRODES

FIELD AND BACKGROUND OF THE INVENTION

The present invention relates to an array of individually addressable micro-electrodes for performing biological, synthetic and diagnostic reactions. Specifically, the present invention can be used for diagnostic assays such as nucleic acid hybridizations or antibody-antigen reactions and for reactions using synthetic molecules such as the preparation of carbohydrate polymers, as well as for other multimolecular reactions.

The detection and monitoring of biomacromolecules, such as nucleic acid chains and proteins, is a growing sector of the clinical diagnostic field which assays human physiological fluids. In particular, recent concern has centered on the necessity of producing large numbers of new assays for specific nucleic acid sequences as the entirety of the human genome becomes sequenced. Furthermore, because the screening of unknown pathogens or elicited immunoglobulins requires assaying a large number of synthetic or natural epitopes, physiological fluid samples are preferably simultaneously reacted with large numbers of epitopes in order to more efficiently diagnose a particular disease or condition. These needs are not currently met by conventional diagnostic techniques.

For example, conventional molecular biological techniques such as Northern blots and DNA sequencing, and immunological techniques such as ELISA, presently require laborious handling procedures by qualified technicians which is often time-consuming and lacking in sensitivity, specificity or reproducibility. Furthermore, relatively few conventional methods of assaying DNA lend themselves to the massively parallel assays which are needed to assay many samples simultaneously.

Such assays have been attempted with nucleic acid hybridization, in which a target nucleic acid sequence is attached to a support, and is then reacted with a complementary probe sequence. Typically, the probe carries a reporter group such as a fluorophore or radioactive label, which is then detected in order to determine if the probe has bound to the target. The equivalent assay for proteins is the microtiter ELISA immunoassay. However, both nucleic acid hybridizations and ELISA immunoassays have a number of drawbacks as currently performed.

First, a relatively high concentration of probe-target complexes must be achieved in order to accurately detect the reporter groups. This in turn requires large amounts of reagents which may be expensive, scarce or both. Second, even relatively miniaturized assays, such as a microtiter ELISA immunoassay, require rather large surface areas for each individual reaction. Thus, performing a massively parallel assay can result in an unacceptably large overall surface area for the entire assay as a whole, which also tends to increase the amount of required reagents.

In order to overcome these problems, recently attempts have been made to miniaturize these assays to the micron level, thereby producing a "chip" which could hold all of the samples needed for one assay in a microscopically small area. Research has been particularly active in the field of nucleic acid hybridization. For example, a number of methods have been described for binding target DNA to a support surface at high densities, and even for synthesizing target DNA or peptide segments directly on a support surface. These methods all enable relatively high density arrays of target material to be prepared for hybridization by complementary DNA or peptidic probes.

In one method, starter oligonucleotides were attached to glass slides [E. M. Southern, *Nuc. Acids Res.*, 22:1368–1373, 1994]. In subsequent synthetic steps, these oligonucleotides were elongated by applying reagents in a defined area. After the synthesis is complete, complementary probes were hybridized to the target DNA on the slide. Similarly, arrays of target DNA were synthesized on aminated polypropylene film using a controlled photodeprotection chemistry and photoprotected N-acyl-deoxynucleoside phosphoramidites [R. Matson, *Anal. Biochem.*, 224:110–116, 1995]. Arrays of peptides have been synthesized on cellulose sheets [R. Frank, *Tetrahedron*, 48:9217–9232, 1992]. Methods which do not include direct synthesis on the support have also been developed, which involve the attachment of PCR products to silylated glass slides [M. Schena, *PNAS*, 93:10614–10619, 1996]. Thus, attempts have been made to increase the density of target DNA or peptides by miniaturizing the size of individual sites in the array.

Unfortunately, none of these methods results in a target material-support complex which is easy to hybridize with a complementary probe. Although the DNA or peptide fragments may be in a high density array, the support itself must still be laboriously handled—washed, incubated with complementary probes and then analyzed with a detection device which can determine if the probe bound to the target. Such miniaturization still does not remove many of the obstacles to easy and rapid examination of samples, including the need to perform many subsequent labor intensive steps. Thus, mere miniaturization through high density arrays is not a complete solution to current analytical needs.

A further step towards obtaining such a solution is the APEX (automated programmable electronic matrix) chip as disclosed in U.S. Pat. No. 5,605,662. APEX is a silicon chip containing an array of many micro-electrodes, each of which has a different DNA segment attached. Electric currents are used to both increase the specificity and efficiency of preparation of the chip, and to increase the specificity and rapidity of the DNA hybridization reaction. The chip can be used as part of a highly automated method of performing DNA hybridization reactions. Unfortunately, the APEX technology is still lacking in a number of aspects.

First, obtaining accurate results with this chip requires a high degree of specificity for the initial attachment of target DNA segments onto the micro-electrodes. Since these micro-electrodes are very small and the resultant array is very dense, such specificity cannot be guaranteed by spatial separation of solutions containing the different target segments. Instead, electronic activation of different micro-electrodes is used to attach specific target DNA segments to different micro-electrodes. However, the remaining electrodes are still available to the target DNA segments during this process. Thus, there is no absolute bar to prevent DNA segments from attaching to more than one electrode simultaneously.

Second, the orientation of the attached DNA segments is not considered. Since the absolute amount of target DNA at each electrode is relatively low, the chip depends upon a relatively high rate of probe/target interactions to enable sufficient signals for determining whether a particular probe bound to a particular target. In any type of reaction which binds target DNA to a support, some of the bound DNA will not be accessible to a complementary probe because of the relative orientation of the target DNA to the probe. Ensuring the proper orientation of the target DNA segments will reduce the amount of inaccessible target DNA. However, U.S. Pat. No. 5,605,662 does not discuss this issue and certainly does not provide any solutions to this important problem. Thus, the efficacy of the technology disclosed in U.S. Pat. No. 5,605,662 could be potentially limited by is the problem of orientation of the target DNA segments.

Finally, U.S. Pat. No. 5,605,662 does not describe a method for detecting the presence of a complementary probe bound to a target DNA segment in any detail. Clearly, the overall miniaturization of the array of target DNA segments, coupled with the relatively low amount of probe molecules which could bind to any one target, makes the issue of detection of binding highly important. Thus, the lack of discussion and description of this issue is a significant problem.

Therefore, there is an unmet need, and it would be highly useful to have, a device for performing hybridizations and other multimolecular reactions and interactions, which employs a high density array of micro-electrodes, which specifically and efficiently binds target material such as DNA segments in a proper orientation, which can easily and rapidly be used for subsequent molecular interactions such as hybridization of complementary probes, and which is part of a system for rapid and sensitive detection of such molecular interactions.

SUMMARY OF THE INVENTION

According to the present invention, there is provided a micro-circuit including: (a) a support; (b) at least one micro-electrode attached to the support, the micro-electrode being selectively electronically activated and the micro-electrode having a protective layer which is removable; (c) a binding entity for attachment to the at least one micro-electrode, the binding entity being capable of attachment to the at least one micro-electrode when the protective layer has been removed; and (d) a power source being operatively connected to the at least one micro-electrode for electronically activating the at least one micro-electrode. Preferably, the micro-circuit includes a plurality of micro-electrodes, and each of the plurality of micro-electrodes has a different binding entity attached. Also preferably, the micro-electrode includes a material selected from the group consisting of gold, aluminum, silver, tin, copper, platinum, palladium, carbon, semiconductor materials and indium tin oxide. Preferably, the support includes a material selected from the group consisting of silicon derivatives, plastic, ceramic and glass. Also preferably, the power source is a direct current source.

According to preferred embodiments of the present invention, the protective layer includes a metallic material. Preferably, the metallic material is copper. More preferably, the metallic material is removed by oxidation following electronic activation of the at least one micro-electrode.

According to another preferred embodiment of the present invention, the micro-circuit further includes an orientation layer, the orientation layer being attached to the micro-electrode, and the orientation layer providing a proper orientation for the binding entity. Preferably, the orientation layer includes molecules formed from a material selected from the group consisting of thiolipid and silylated lipid. More preferably, the molecules feature a hydrocarbon backbone substituted with at least one functional moiety selected from the group consisting of (1,3)-diyne, amide and urethane. Most preferably, the functional moiety of the hydrocarbon backbone is capable of polymerization, such that a covalent bond is formed between at least two of the molecules. Alternatively and preferably, the functional moiety of the hydrocarbon backbone is capable of forming a hydrogen bond, such that a non-covalent bond is formed between at least two of the molecules. Also preferably, the molecules are polyoxymethylene substituted with a functional moiety selected from the group consisting of sulfur, disulfide and silicon derivatives.

According to yet another preferred embodiment of the present invention, the micro-circuit further includes a reservoir for holding a substantially liquid buffer such that the buffer is able to contact the at least one micro-electrode.

According to still another preferred embodiment of the present invention, the micro-circuit further features a complementary probe for interacting with the binding entity, the probe featuring a reporter molecule, such that an interaction of the probe with the binding entity is detectable. Preferably, the micro-circuit further includes a micro-circuit reader for detecting the interaction of the probe with the binding entity. More preferably, the reporter molecule is a fluorophore, the micro-circuit reader includes a light source for producing light and exciting the fluorophore, and the micro-circuit reader includes a detector for detecting emitted light from the fluorophore. Also preferably, the light source is selected from the group consisting of Xenon lamp, laser and monochromator, and the detector is selected from the group consisting of photomultiplier tube, charge-coupled device camera and multianode photomultiplier tube. Most preferably, the micro-circuit reader further comprises a microlens, the microlens focusing the light produced by the light source substantially on the micro-electrode, and the microlens focusing the emitted light on the detector. Alternatively and preferably, the micro-circuit reader further comprises a beam splitter, the beam splitter permitting the light produced by the light source to reach the micro-electrode, and the beam splitter reflecting the emitted light at an angle such that the emitted light is detectable by the detector. Also alternatively and preferably, the micro-circuit reader further comprises a coupler, such that the micro-circuit reader is capable of detecting the interaction of the probe with the binding entity from a plurality of micro-electrodes.

Preferably, the binding entity is selected from the group consisting of oligodeoxyribonucleic acids, ribonucleic acids, synthetic oligonucleotides, peptides, peptide nucleic acids, polypeptides, proteins, enzymes, antibodies such as polyclonal, monoclonal, catalytic, single domain and Fab' fragments, immunoadhesins, lectins, glycoproteins, receptors, natural and synthetic polysaccharides, synthetic polymers, molecular imprints, ligands, chelates, viruses, ligands to cell receptors, chelates and phage display libraries.

According to another embodiment of the present invention, there is provided a method for specifically attaching a binding entity to at least one of a plurality of micro-electrodes, each of the micro-electrodes being selectively electronically activatable, the method including the steps of: (a) coating the micro-electrodes with a protective layer to form protected micro-electrodes; (b) electronically activating at least one of the protected micro-electrodes to remove the protective layer and to form at least one deprotected micro-electrode; and (c) contacting the binding entity with the at least one deprotected micro-electrode such that the binding entity is specifically attached to the at least one deprotected micro-electrode.

According to still another embodiment of the present invention, there is provided a detection system for detecting an emission of light from a fluorescent moiety on a plurality of micro-electrodes of a micro-electrode array, the system including: (a) a light source for exciting the fluorescent moiety, such that the fluorescent moiety emits the light from each of the plurality of micro-electrodes; (b) a separator for separating the light emitted from each micro-electrode, such that the light is separated micro-electrode light; and (c) a detector for detecting the separated micro-electrode light for each micro-electrode. Preferably, the separator and the detector are combined in a CCD camera. Also preferably, the light source is selected from the group consisting of Xenon lamp, laser and monochromator.

According to preferred embodiments of the present invention, the detector is selected from the group consisting of photomultiplier tube and multianode photomultiplier tube. Preferably, the micro-circuit reader further comprises a microlens, the microlens selectively focusing the light produced by the light source substantially on each of the micro-electrodes, and the microlens selectively focusing the emitted light on the detector.

According to other preferred embodiments of the present invention, the micro-circuit reader further comprises a beam splitter, the beam splitter permitting the light produced by the light source to reach each of the micro-electrodes, and the beam splitter reflecting the emitted light at an angle such that the emitted light is detectable by the detector. Also preferably, the micro-circuit reader further comprises a coupler, such that the micro-circuit reader is capable of detecting the interaction of the probe with the binding entity from each of the plurality of micro-electrodes.

According to yet another embodiment of the present invention, there is provided a method of performing a nucleic acid hybridization assay, including the steps of: (a) providing a micro-circuit, the micro-circuit featuring: (i) a support; (ii) a plurality of micro-electrodes attached to the support, the micro-electrodes being selectively electronically activatable and the micro-electrodes having a protective layer which is removable; (iii) a binding entity for attachment to at least one of the plurality of micro-electrodes, the binding entity being capable of attachment to the at least one of the plurality of micro-electrodes when the protective layer has been removed and when the at least one of the plurality of micro-electrodes is electronically activated; and (iv) a power source being operatively connected to the at least one micro-electrode for electronically activating the at least one of the plurality of micro-electrodes; (b) removing the protective layer from the at least one of the plurality of micro-electrodes; (c) electronically activating the at least one of the plurality of micro-electrodes; (d) contacting the at least one nucleic acid binding entity with the at least one of the plurality of micro-electrodes, such that the at least one nucleic acid binding entity becomes attached to the at least one of the plurality of micro-electrodes; (e) contacting the plurality of micro-electrodes with a probe for binding to the nucleic acid binding entity, such that the probe becomes bound to the nucleic acid binding entity; and (f) detecting a presence of the probe bound to the nucleic acid binding entity.

Preferably, the nucleic acid binding entity is selected from the group consisting of RNA and DNA molecules. More preferably, the probe is selected from the group consisting of RNA and DNA molecules.

BRIEF DESCRIPTION OF THE DRAWINGS

The invention is herein described, by way of example only, with reference to the accompanying drawings, wherein.

DESCRIPTION OF THE INVENTION

Figure 1:
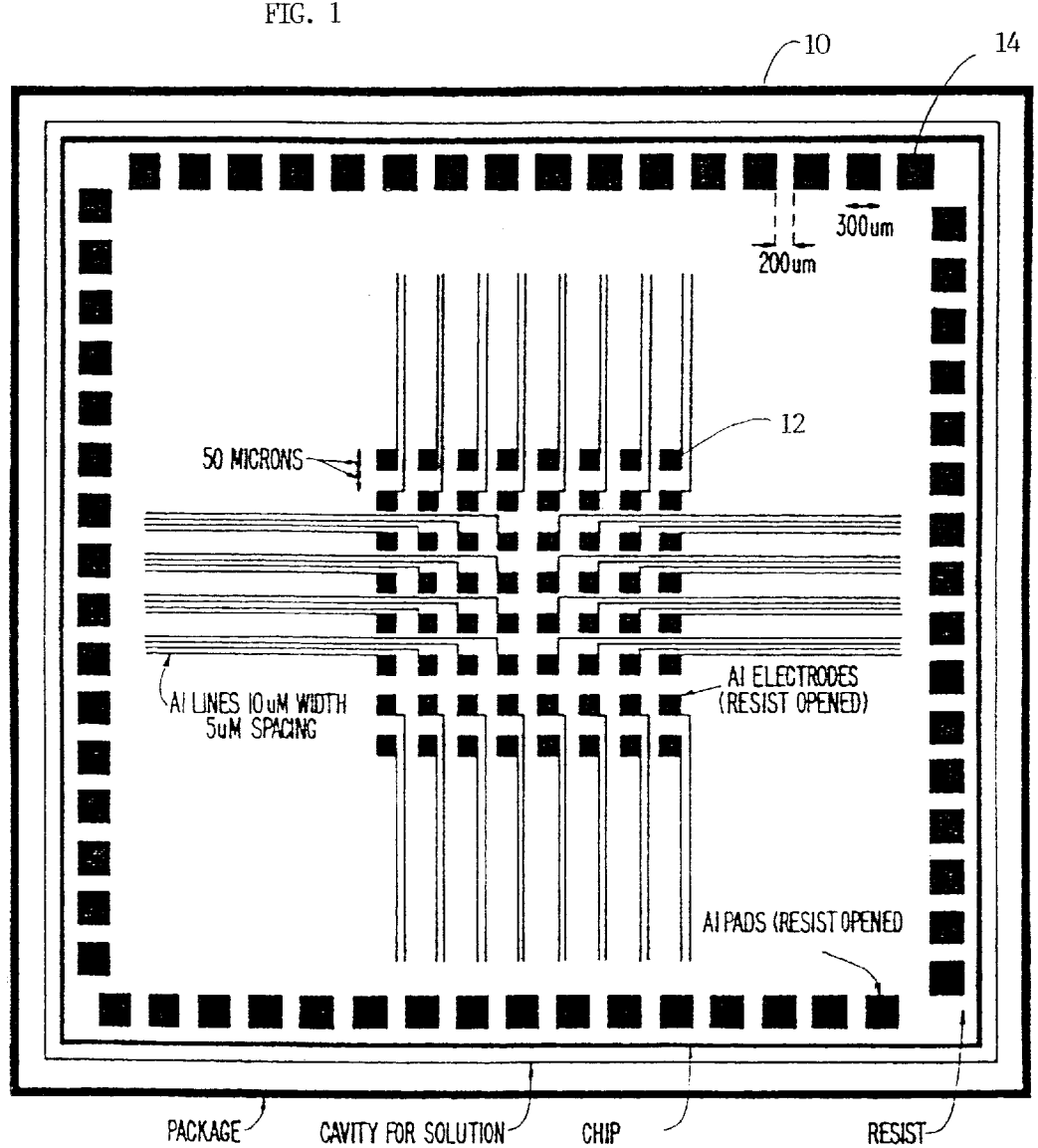
FIG. 1 is an illustration of an exemplary prior art micro-electrode chip.

The present invention is of a device for performing biological and diagnostic reactions, as well as of methods of constructing and using the device of the present invention. This device is a microelectronic device with separately addressable microscopic locations featuring a microscopic electrode (hereinafter referred to as "micro-electrode" for brevity) which is protected until it is desired to attach a binding entity to a specific micro-electrode or micro-electrodes. At the time of attachment, one or more micro-electrodes is deprotected, enabling the binding entity to form, for example, a covalent bond to the deprotected micro-electrode or micro-electrodes. The particular advantage of the cycle of protection and deprotection is that extremely high specificity of binding of the binding entity to the desired micro-electrode or micro-electrodes can be achieved.

An analogy can be drawn to the common practice in synthetic chemistry of adding "protecting" groups, or chemical moieties, to those portions of a molecule which might react undesirably with another molecule during a synthetic procedure. Although the chemical reaction could still be performed in the absence of these protecting groups, the lack of specificity of the reaction would prove highly detrimental to the entire synthetic process. Similarly, it is contemplated that the cycle of protection and deprotection of micro-electrodes of the present invention provides such a high degree of specificity, thereby greatly increasing both the efficiency of assembly of the device of the present invention, and the ability of the device of the present invention to successfully perform biological and diagnostic reactions.

The basic assembly of the micro-circuit of the present invention is as follows. Microfabrication techniques based on wet or dry etching combined with photolithographic processes are widely used for the preparation of two-dimensional electronic micro-circuits, such as the device of the present invention. One example of such a circuit is a glass or polymeric surface covered with a direct current (DC) electrode array, which can be an indium tin oxide micro-electrode array or a gold micro-electrode array. In the device of the present invention, each micro-electrode is preferably separately activatable or "addressable", although a group of such electrodes could also be collectively addressable. Hereinafter, the term "array" includes any arrangement of micro-electrodes of the device of the present invention. The micro-electrodes can be arranged in two-dimensional arrays, three-dimensional arrays or other array formats. Preferably, the micro-electrodes are arranged on a supportive surface in a regular two-dimensional array.

Once the micro-circuit has been assembled, according to techniques known in the art and briefly described below, the micro-electrodes are protected by the addition of a protective layer, which is preferably a metallic substance such as copper. Next, each micro-electrode (if separately addressable), is separately and individually activated to remove the protective layer (hereinafter referred to as "deprotection"). Finally, the desired specific binding entity is attached to the electrode, preferably by a covalent bond.

An additional derivatization step is optionally included either after the protection step or the deprotection step, depending upon the desired effect of the derivatization. For example, the micro-electrode can be derivatized with a spacer molecule which then forms a covalent bond with the binding entity. As described in further detail subsequently, the spacer molecule can also keep the binding entity in the proper orientation for interaction with a second molecule such as a complementary probe. The spacer molecule can also provide greater stability for the binding entity/micro-electrode complex. Both of these objectives can be accomplished through the formation of either covalent or non-covalent bonds between the spacer molecules. These spacer molecules can be collectively described as an "orientation layer" for their ability to properly orient the binding entities. Thus, the derivatization step can improve both the stability and the functionality of the final micro-circuit.

Once constructed, the micro-circuit of the present invention is able to actively perform multi-step, combinatorial and multiplex reactions and syntheses, and multimolecular interactions, at any of its micro-electrodes. Specifically, potential multimolecular interactions include, but are not limited to, oligonucleotide hybridizations and antibody-antigen interactions. Examples of synthetic reactions include, but are not limited to, syntheses of biological and synthetic polymers such as peptides, oligonucleotides and carbohydrates. Hereinafter, the term "multimolecular" includes interactions and/or reactions between at least two or more molecules, either sequentially or substantially simultaneously.

A more detailed description of both the assembly and the use of the device of the present invention can be found in the section entitled "Detailed Description of the Invention", which has a number of subsections. The first subsection, "Prior Art Micro-circuit", shows how a prior art micro-circuit is constructed. The second subsection, "Construction of the Micro-circuit of the Present Invention", shows both the design of the device of the present invention and several examples of methods of construction. The third subsection, "Applications of the Micro-circuit of the Present Invention", describes how the device of the present invention provides electronic control of various multi-step, combinatorial and multiplex reactions, and multimolecular interactions, as well as specific diagnostic assays and synthetic reactions which can be performed with this device.

Hereinafter, the term "micro-electrode", unless otherwise stated, refers to an electrode biased either positively or negatively, which is capable of operating in a direct current mode (either continuous or pulse), which can affect or cause the free field electrophoretic transport of charged specific binding entities, reactants or analytes to or from substantially any location on the device, or in the sample solution contacting the device. Within the scope of this invention, the free field electrophoretic transport of molecules is not dependent on the electric field produced being bounded or confined by dielectric materials.

Hereinafter, the term "binding entity" refers to a biological or synthetic molecule that has a specific affinity to at least one other atomic element or molecule, through covalent or non-covalent bonding. The binding entity is also capable of attachment to the micro-electrode, either through a non-covalent, but preferably through a covalent, bond. Preferably, the binding entity contains a functional chemical group, a common nucleic acid sequence, a peptidic or carbohydrate epitope (such as an antigen or hapten), or a ligand that allows it to bind to a common functional group on the surface of a micro-electrode. Binding entities include, but are not limited to, oligodeoxyribonucleic acids, ribonucleic acids, synthetic oligonucleotides, peptides, peptide nucleic acids, polypeptides, proteins, enzymes, antibodies such as polyclonal, monoclonal, catalytic, single domain and Fab' fragments, immunoadhesins, lectins, glycoproteins, receptors, natural and synthetic polysaccharides, synthetic polymers, molecular imprints, ligands, synthetic or natural ligands to cell receptors, chelates, viruses and phage display libraries.

Hereinafter, the term "peptide nucleic acids" designates a class of chemicals which are structurally similar to DNA or RNA segments and which are able to hybridize strongly to complementary single stranded DNA or RNA segments, yet which substantially lack the ribose units of DNA or RNA.

DETAILED DESCRIPTION OF THE INVENTION

The present invention is of an electronic device which includes an array of micro-electrodes, each of which is preferably separately and individually activatable, to which at least one type of binding entity can be attached. Each micro-electrode is first protected by the attachment of a protective material, and then deprotected by the removal of this material when the binding entity is to be bound to the micro-electrode. The advantage of this cycle of protection and deprotection is that it provides greatly enhanced specificity of attachment of the binding entity to the micro-electrode. As described further below, the present invention also includes an optional orientation layer for stabilizing and orienting the binding entities and a micro-reader for detecting an interaction between a complementary probe and the binding entities, as well as methods for constructing and using the device of the present invention in a number of assays.

PRIOR ART MICROCIRCUIT

As noted previously, the construction of the micro-circuit of the present invention partly uses techniques which are well known in the prior art. For the purposes of description only and without any desire to be limiting, an example is given herein of the construction of such a prior art micro-circuit, as a demonstration of these well known techniques. This exemplary prior art micro-circuit was disclosed in U.S. Pat. No. 5,605,662, which describes a number of these well known techniques and is herein incorporated by reference for descriptive purposes only.

FIG. 1 shows the prior art chip of U.S. Pat. No. 5,605,662. A chip 10 has 64 micro-electrodes 12. The disclosed chip 10 is described as being a square of 1.5 centimeters by 1.5 centimeters, with a central area of 750 microns by 750 microns containing the 64 micro-electrodes 12. Connective circuitry for each individual micro-electrode runs to an outside perimeter of metal contact pads 14.

As disclosed in U.S. Pat. No. 5,605,662, chip 10 is constructed using standard photolithography techniques and a simple mask design. The base substrate material is a silicon wafer or chip. A simplified explanation of the method of construction is provided herein as an example only and is not meant to be limiting in any way.

A silicon dioxide ($SiO_2$) coat is first applied to the substrate chip by plasma enhanced chemical vapor deposition (PECVD). Next, a metal layer is deposited by vacuum evaporation. The metal is any suitable metal such as aluminum, gold, silver, tin, copper, platinum, palladium, carbon and various metal combinations.

In subsequent steps, the chip is coated with a positive photoresist, then masked with the circuitry pattern, exposed and developed. The photo-solubilized resist is removed and the exposed aluminum is etched away. The resist island is then removed, leaving the metal circuitry pattern on the chip, including metal contact pads 14, connective wires and the center array of micro-electrodes 12.

Finally, again using plasma enhanced chemical vapor deposition, two additional layers of silicon dioxide and silicon nitride are added for insulation and sealing. As previously, chip 10 is coated with a positive photoresist, masked for contact pads 14 and micro-electrodes 12, exposed and developed. The photo-solubilized resist is removed and the exposed aluminum is etched away to expose contact pads 14 and micro-electrodes 12. After the island resist is removed, the connective wiring between contact pads 14 and micro-electrodes 12 remains insulated by silicon dioxide and silicon nitride. Micro-electrodes 12 of the prior art chip 10 are now ready for further modifications which are described below.

Construction of the Micro-circuit of the Present Invention

The micro-circuit of the present invention represents a significant improvement over the prior art chip described in FIG. 1. The advantages of the micro-circuit of the present invention include greater specificity of attachment of the binding entities to the micro-electrodes, as well as preferably enabling the binding entities to be presented with the proper orientation to increase the efficiency of subsequent multi-molecular interactions. These advantages are obtained through the additional construction and preparation steps detailed below, which start with the prior art chip of FIG. 1 only as an exemplary base. For a greater understanding of these additional steps, a few general aspects of the micro-circuit of the present invention are described herein.

The micro-circuit of the present invention can have as few as two addressable micro-electrodes, and as many as hundreds of thousands of micro-electrodes or more. A complex micro-circuit, with many micro-electrodes, would preferably be constructed using microlithography techniques. The construction is performed on a suitable substrate material such as silicon, glass, silicon dioxide, plastic or ceramic materials. Alternatively and preferably, less complex micro-circuits could be constructed using micro-machining techniques.

Addressable micro-electrodes can be of any shape, preferably round, square or rectangular. An addressable micro-electrode can also be any size, preferably ranging from sub-micron to several centimeters, with from about 5 microns to about 100 microns being the most preferred size range for devices constructed by microlithography techniques, and from about 100 microns to about 5 millimeters being the most preferred size range for devices constructed by micro-machining techniques. If micro-electrodes of a smaller size than that obtainable from microlithography techniques are desired, other techniques such as electron beam lithography, ion beam lithography or molecular beam epitaxy. While microscopic locations are desirable for analytical and diagnostic type applications, larger addressable locations such as those of at least about 2 millimeters in size are desirable for preparative scale synthetic reactions or purification techniques.

One important characteristic of the size and distribution of micro-electrodes is that there should not be any interaction between molecules at different sites.

As noted previously, one important aspect of the device of the present invention is that each micro-electrode is first protected and then deprotected during the process of attaching the binding entities to the micro-electrode. One example of performing such a cycle of protection and deprotection is described below, it being understood that this is intended only as an example and is not meant to be limiting in any way.

EXAMPLE 1

Step 1

The first step involves protection of the micro-electrodes of the micro-circuit of the present invention by coating or covering the micro-electrodes with some protective material, such as a metallic substance, for example. Optionally, the micro-electrode could be additionally protected with a layer of an alkylthiol or a corresponding disulfide. If the micro-electrodes are made from gold, then the protective material is preferably copper. One preferred method of covering the electrodes involves electrodeposition.

Electrodeposition requires the micro-electrode to be electronically activated while contacting a copper-containing solution. For example, the micro-electrode could be placed in a bath which contains a solution of copper sulfate. A counter electrode, such as a platinum wire, and a reference electrode, such as a saturated calomel electrode, would also need to be placed in the bath, forming an electrochemical cell. The electricity current exchanged in the electrochemical cell would determine the thickness of the electrodeposited layer of copper on the micro-electrode. Thus, copper could be deposited on a gold micro-electrode in a controlled manner by this method.

Alternative methods for the controlled deposition of copper on a gold electrode involve electroless plating or vapor deposition. The technique of electroless plating involves the deposition of metal using an electroreductive or oxidative process through the application of particular chemical compositions in solution. Copper bath compositions suitable for electroless plating include, but are not limited to, the following aqueous solutions of copper sulfate: 2 g $CuSO_4$, 4 g NaOH, 1 ml 25% $NH_3$, 3.5 ml glycerol, 8–15 ml 10% $CH_2O$ with water up to 100 ml; or 150–200 g $CuSO_4$, 7–25 g 12 M $H_2SO_4$, 30–50 ml $CH_2H_5OH$ with water up to 1000 ml.

Vapor deposition is used to deposit a thin layer of metal on a metallic surface by using an ultra-high vacuum to facilitate this deposition.

Optionally, after the electrodeposition of copper, another layer could be added to the micro-electrode. This additional layer would be a self-assembled mono-layer of an alkylthiol or a corresponding disulfide of a generic structure R—SH or R—SS—R, where R can be an aromatic moiety, an alkyl moiety or any combination of these moieties, and S is a sulfur atom. These compounds can also be described as "thiolipids", and the additional layer as a lipid layer.

Preferably, this layer is added by contacting the copper-protected electrode with a solution containing the desired alkylthiol or corresponding disulfide. For example, the alkylthiol or corresponding disulfide could be present in a 1 mM concentration in ethanol or any type of organic solvent. The contact time could be varied from 1 minute to 1 day, depending upon conditions (see Ullman, Abraham, *Chem. Rev.*, 96:1553–1554, 1996). A wide range of suitable temperatures can be employed, ranging from about 0 to about 100 degrees Celsius.

After contacting the copper-covered electrode with this solution, the micro-electrode would be further covered and passivated in a chemisorption reaction. Chemisorption is a surface phenomenon in which strong chemical bonds are established between reactants. These bonds are energetically strong enough to be on the order of magnitude of the strength of covalent bonds, yet these bonds are not actually true covalent bonds.

The chemisorption reaction on the micro-electrode is enabled by the strong chemisorption energy of species of the general formula $RS^-Au^+(Au^0)_n$. This chemisorption energy is in the range of about 40–45 kcal/mole. The general properties of self-assembled monolayers formed according to such a chemisorption process are well known in the literature [D. Mandler and I. Turyan, *Electroanalysis*, 8:207–213, 1996; D. L. Allara, *Biosensors & Bioelectronics*, 10:771–783, 1995; C. Buess-Herman, *Progress in Surface Science*, 46:335–375, 1994; M. Mrksich and G. M. Whitesides, *Ann. Rev. Biophys. Biomol. Struct.*, 25:55–78, 1996; and A. Ulman, *Chem. Rev.*, 96:1533–1554, 1996]. Essentially, such self-assembled monolayers are known to be stable and irreversible for all intents and purposes.

Preferably, the chemical structures of these passivating sulfur-based lipid-like reagents could be additionally modified to provide such properties as ionic and solvent permeability and controlled chemical stabilities by forming two-dimensional hydrogen bond-based arrays.

Figure 2:
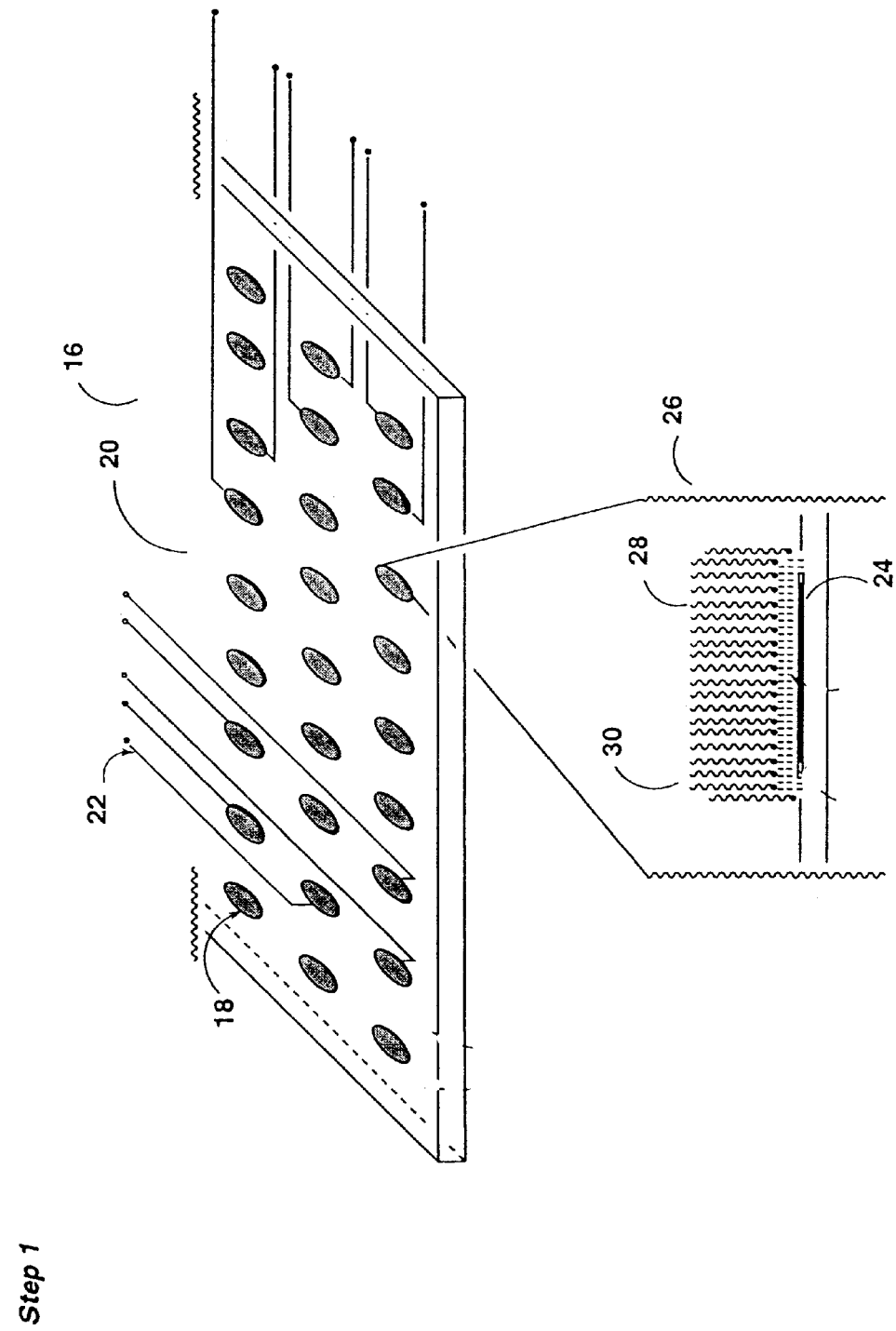
FIG. 2 shows the micro-circuit of the present invention after the protection step.

FIG. 2 shows a portion of an exemplary micro-circuit according to the present invention after both the protective layer and the additional, optional lipid layer. A micro-circuit 16 has a plurality of micro-electrodes 18 arranged on a support surface 20. Conducting wires 22 are attached to micro-electrodes 18. Each micro-electrode 18 is protected by a protective layer 24, in this case copper. An enlargement 26 of a portion of one micro-electrode 18 shows a plurality of thiolipid molecules 28 forming lipid layer 30.

Step 2: Deprotection

In order to attach the binding entity to the micro-electrode, the surface of that electrode must be available for a chemical reaction in which the binding entity itself, or an additional reactive moiety, is bound to the surface of the micro-electrode either directly or indirectly through an additional functional group. The process by which the surface of the micro-electrode becomes available for such a chemical reaction is termed "deprotection" herein, and involves either the removal or the alteration of the protective layer which was added in Step 1 previously. Although electrochemical deprotection of the micro-electrode is described in this example, it is understood that this description is for illustrative purposes only and that many other types of chemical reactions could be suitable for deprotection of the micro-electrode, depending upon the type of protective layer which was added in Step 1.

In the preferred embodiment of Step 2, the micro-electrode to be deprotected is placed in buffered aqueous media. Next, the micro-electrode is electronically activated. The resultant oxidative process causes the metallic layer, in this copper, to become removed from the micro-electrode. If the copper layer has been optionally further derivatized with a thiolipid layer, such a layer would also be removed with the copper. In any case, the surface of the micro-electrode itself becomes exposed. In this example, since the micro-electrode is preferentially gold, the gold metal becomes exposed and available for a chemical reaction.

As noted previously, one particular advantage of this method is that substantially the entirety of the micro-circuit can be placed in the aqueous media at one time, yet, if desired, each micro-electrode can be individually deprotected. Such selectivity is possible if each micro-electrode is separately, individually electronically activatable, since the micro-electrode must be electronically activated in order to become deprotected. Thus, if only one micro-electrode is electronically activated, only that micro-electrode will become deprotected and available for attachment of the binding entity.

Figure 3:
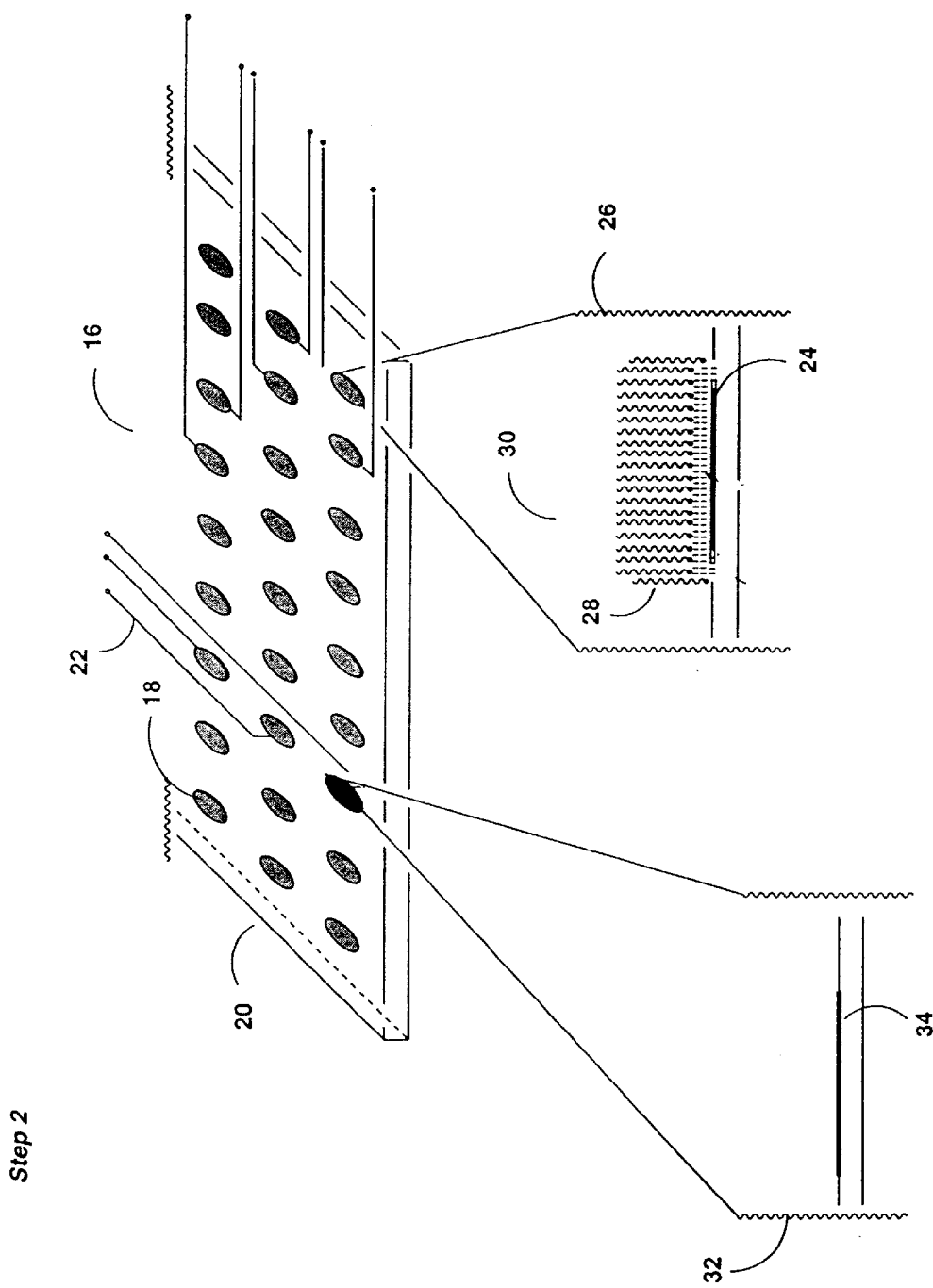
FIG. 3 shows the micro-circuit of FIG. 2 after deprotection.

FIG. 3 shows the portion of the exemplary micro-circuit of FIG. 2 according to the present invention after both the protective layer and the additional, optional lipid layer have been substantially removed. A portion of micro-electrode 18 has been deprotected, as shown in an enlargement 32, exposing gold surface 34.

Step 3: Attachment of Binding Entity

Once the micro-electrode has been deprotected, it is available for attachment of the binding entity. As noted previously, such attachment can either be a direct bond between the binding entity and the surface of the micro-electrode, or an indirect bond between a reactive moiety on the binding entity and/or a reactive moiety on the surface of the micro-electrode. In this example, since the micro-electrode is gold, preferably the binding entity is derivatized with a thiol functional group as the reactive moiety. As noted previously, sulfur reacts with gold to form a substantially permanent bond in a chemisorption reaction. Thus, the reactive sulfur moiety on the binding entity would form a strong bond with the gold surface of the micro-electrode.

The binding entity would need to be incubated with the micro-electrode under appropriate conditions to permit attachment of the binding entity to the micro-electrode. For example, if the micro-electrode had a gold surface, and the binding entity had a reactive thiol group, the attachment process would simply require placing the binding entity in an appropriate solvent such as ethanol-water mixtures in various ratios, and then enabling the solvent to contact the micro-electrode surface. Preferably, the mixture would be degassed with nitrogen substantially before the binding entity is placed in the solvent. This process could be repeated for each micro-electrode for which such attachment is desirable. If substantially each and every micro-electrode has a unique binding entity attached, the resultant microcircuit will have an array of unique entities, hereinafter referred to as a "binding entity array".

Figure 4:
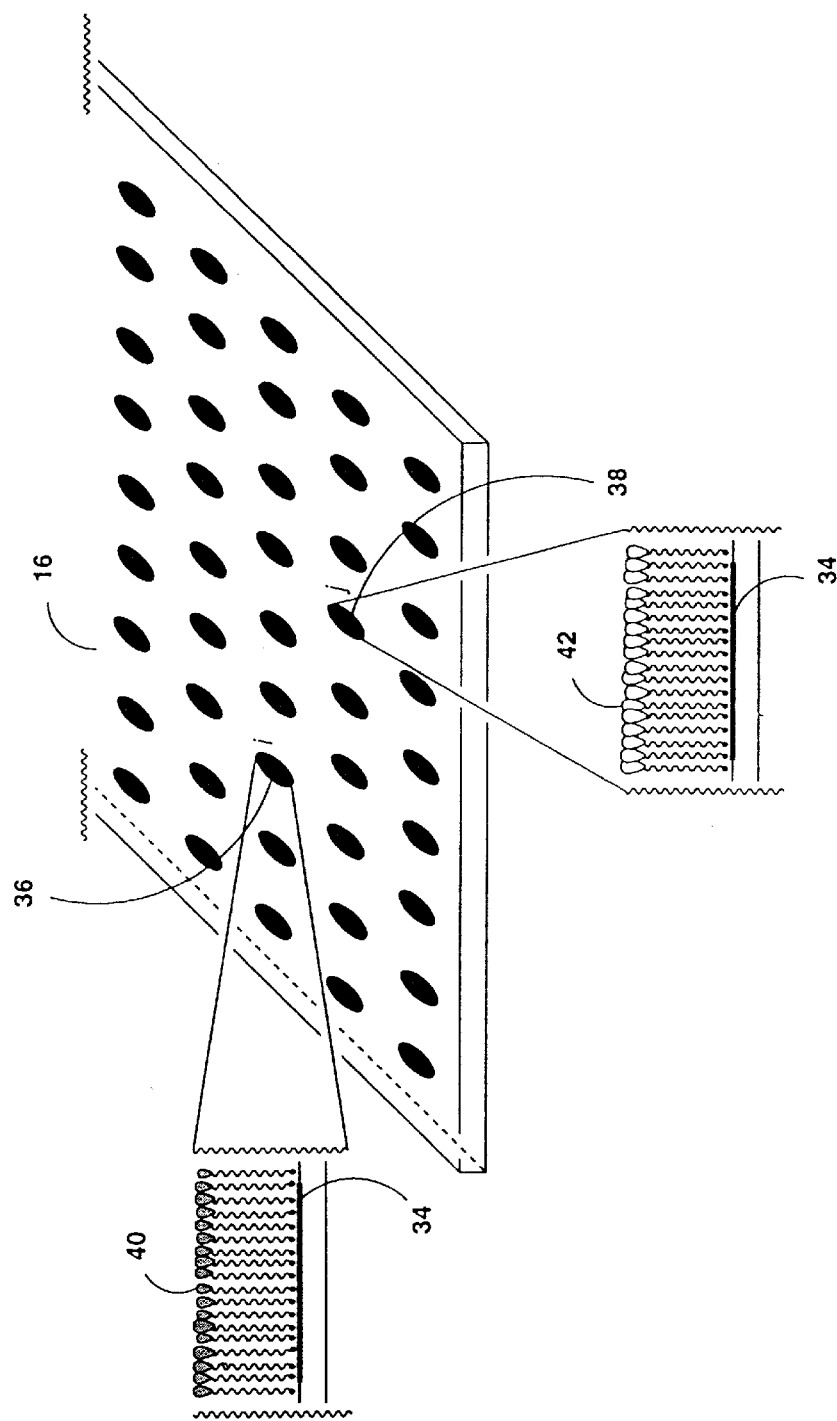
FIG. 4 shows the micro-circuit of FIG. 3 after the attachment of binding entities.

FIG. 4 shows an example of a micro-circuit of the present invention with a plurality of oligonucleotides as the binding entities. Micro-circuit 16 has a first micro-electrode 36 and a second micro-electrode 38. First micro-electrode 36 has a plurality of oligonucleotides i 40 bound to gold surface 34. Second micro-electrode 38 has a plurality of oligonucleotides j 42 bound to gold surface 34. Preferably, oligonucleotides i 40 and j 42 have different sequences or are otherwise not identical. Both oligonucleotides i 40 and j 42 can be attached to gold surface 34 by a reactive sulfur moiety, as described below.

Figure 5A:
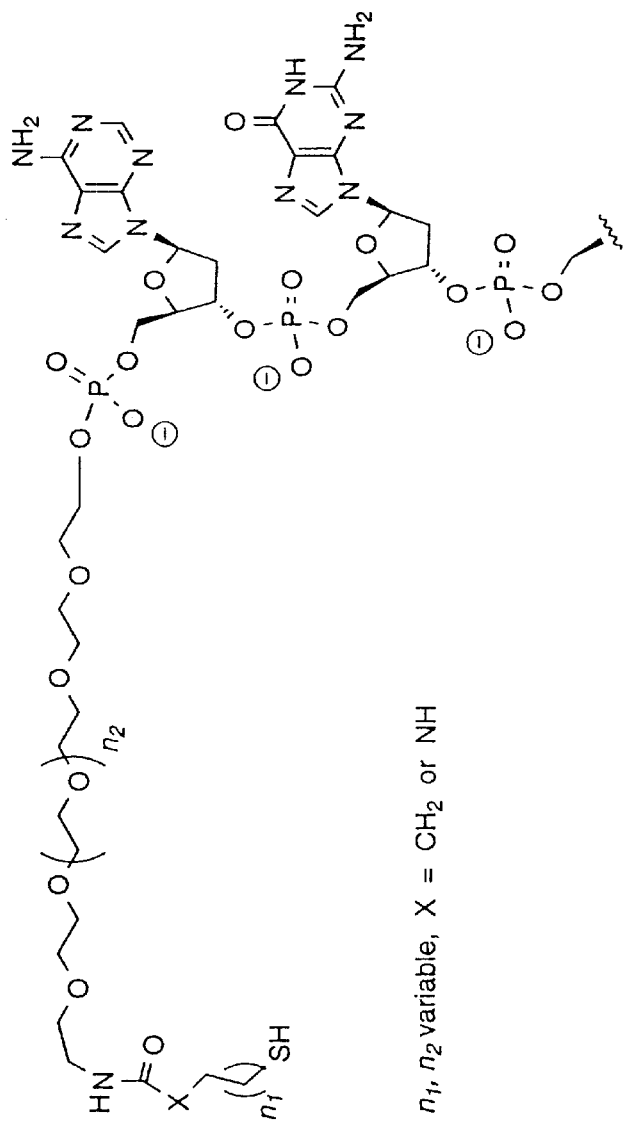
FIGS. 5A–5C illustrate examples of binding entities with suitable reactive groups for attachment to the micro-circuit of FIG. 4.
Figure 5B:
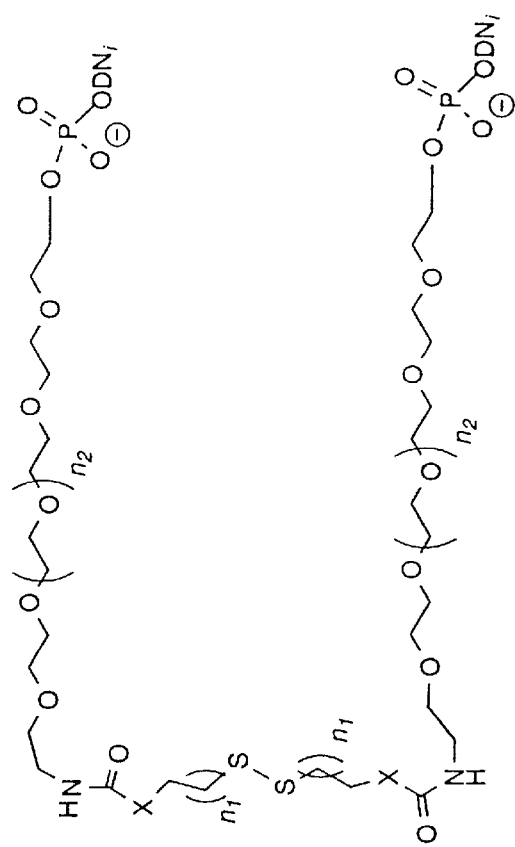
Figure 5C:
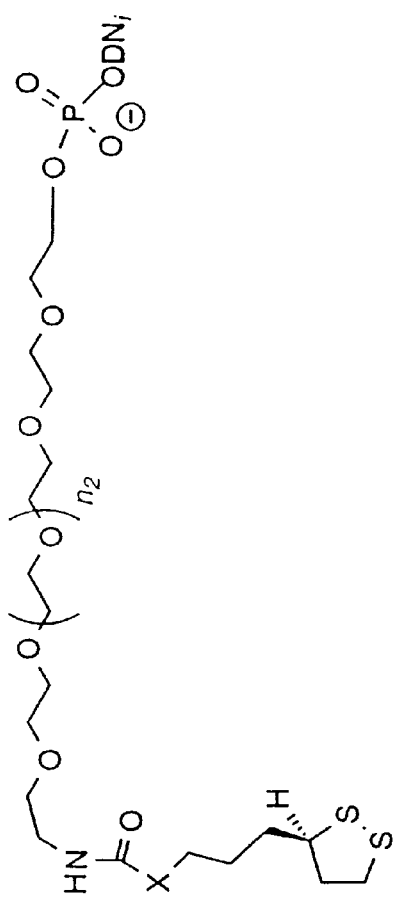

For the purposes of illustration only, a number of different examples of binding entities with reactive sulfur moieties are shown in FIGS. 5A–5C. These binding entities are oligodeoxynucleotide probes, it being understood that any of the other types of binding entities could be substituted after suitable adjustments to the functional group containing the reactive sulfur moiety.

FIG. 5A shows oligodeoxynucleotide probes with structures of type A having the general formula R—SH, in which R is the oligodeoxynucleotide probe itself. Optionally, R can be the probe with an additional spacer arm to which the sulfur moiety is attached. Structures of type A are true thiols. A portion of a thiol modified oligodeoxynucleotide is shown, including a core oligodeoxynucleotide. Core oligodeoxynucleotide can be of substantially any length, although only two bases are shown. A polyoxymethylene spacer has been added at the 5' position of thiol modified oligodeoxynucleotide, although polyoxymethylene spacer could also have been added at the 3' end of core oligodeoxynucleotide. Polyoxymethylene spacer has a thiol function at one end. Polyoxymethylene spacer thus has the general formula $[(CH_2)_2O]_{n2}$—$(CH_2)_2$—NH—C(=O)—X—$(CH_2)_{n1}$—SH, in which $n_1$ and $n_2$ are variable and X is either $CH_2$ or NH.

FIG. 5B shows oligodeoxynucleotide probes with structures of type B1 having the general formula R—SS—R', in which R and R' are each oligodeoxynucleotide probes, which may be different but are preferably substantially identical. Optionally, one or both of R and R' can be the probe with an additional spacer arm to which the sulfur moiety is attached. Structures of type B1 are disulfides. A portion of such a disulfide double oligonucleotide is shown, with two core oligonucleotides. Each core oligodeoxynucleotide can be of substantially any length, although only two bases are shown. The group "$ODN_i$" represents any further oligodeoxynucleotide bases which may be present. Similarly to the thiol structure of FIG. 5A, the core oligonucleotides can be derivatized at either the 3' end or the 5' end of the molecule, with polyoxymethylene space of FIG. 5A for example.

FIG. 5C shows oligodeoxynucleotide probes with structures of type B2 which are disulfide compounds based upon lipoic acid. A portion of a thiol modified oligodeoxynucleotide is shown, including a core oligodeoxynucleotide. Core oligodeoxynucleotide can be of substantially any length, although only two bases are shown. Polyoxymethylene spacer has again been added at the 5' position of core oligodeoxynucleotide, although polyoxymethylene spacer could also have been added at the 3' end of core oligodeoxynucleotide. The thiol function of polyoxymethylene spacer is actually a disulfide group, preferably either an amide or a urethane functional group as shown.

Figure 6:
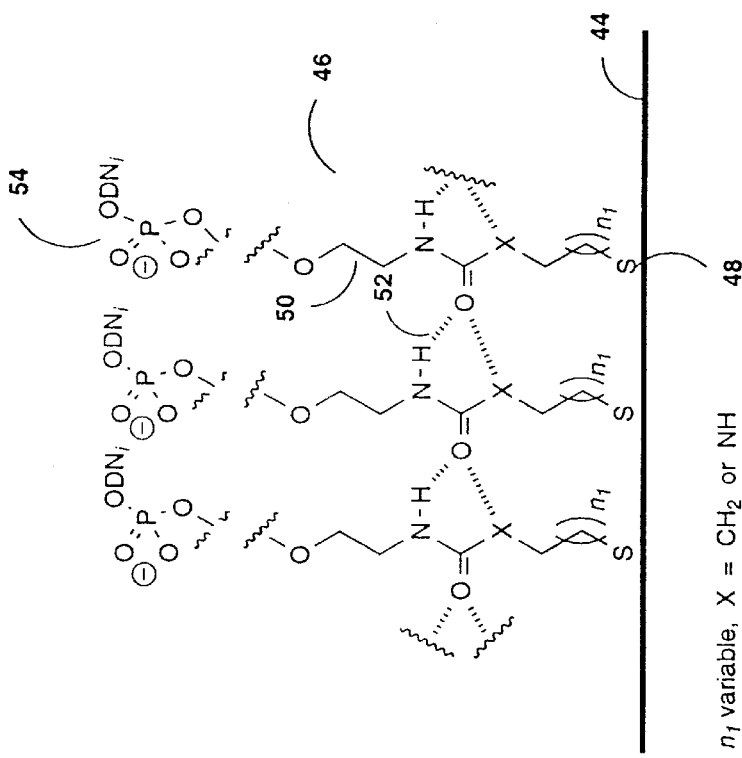
FIG. 6 shows the binding entities of FIG. 5 attached to the surface of a micro-electrode according to the present invention.

FIG. 6 shows a portion of a micro-electrode having oligodeoxynucleotide probes attached to its surface. A portion of an outer surface of a micro-electrode 44 is shown. A plurality of oligonucleotides 46 are bound to outer surface 44 by a sulfur atom 48. Sulfur atom 48 is attached to oligodeoxynucleotide probes 46 by a polyoxymethylene functional group 50, such as that of FIG. 5A. Oligodeoxynucleotides 46 could be those of FIGS. 5A or 5B, for example. As in FIG. 5B, the group "$ODN_i$" represents any further oligodeoxynucleotide bases which may be present.

The advantage of using polyoxymethylene functional group 50 is clearly demonstrated in FIG. 6. As shown, a plurality of hydrogen bonds 52 are formed between polyoxymethylene functional groups 50 attached to different core oligodeoxynucleotides 54, resulting in a two-dimensional array of hydrogen-bonded structures. These hydrogen bonds 52 increase the stability of the entire micro-electrode-bound oligodeoxynucleotides 46, as well as stabilizing the proper orientation of oligodeoxynucleotides 46 relative to the complementary probe molecule which is used in the subsequent hybridization assay (not shown).

EXAMPLE 2

In addition to the method given in Example 1 for preparing a microcircuit having micro-electrodes to which binding entities are attached, a second exemplary method is described in this Example, it being understood that this is for illustrative purposes only and is not meant to be limiting. In this method, the spacer arm molecules which form the hydrogen-bonded monolayer are attached to the micro-electrode surface first, and then the binding entity is attached directly to the spacer arm molecules themselves rather than to the micro-electrode surface as in Example 1.

Figure 7:
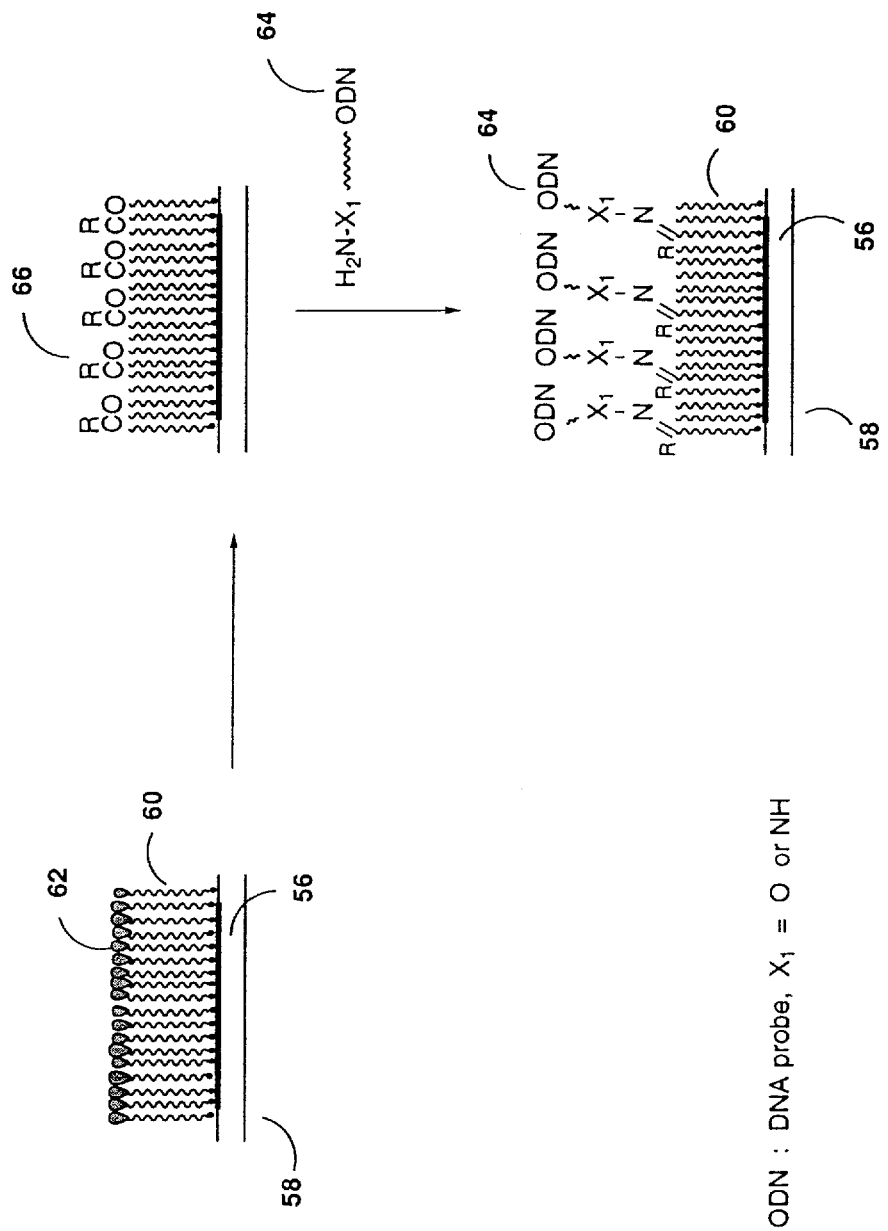
FIG. 7 shows an alternative method of attaching binding entities to the surface of a micro-electrode according to the present invention.

The method of Example 2 has the same first two steps as that of Example 1. Step 3, however, is different and is broken into two parts, as illustrated in FIG. 7. In Step 3a, the spacer arm molecules are attached to the micro-electrode surface. In Step 3b, the binding entity is attached directly to the spacer arm molecules themselves. Optionally, the spacer arm molecules can be further derivatized before attachment of the binding entity, in a step intermediate to Steps 3a and 3b. The net result, however is similar to the method of Example 1: a micro-circuit having an array of micro-electrodes to which a binding entity is attached.

Step 3a: Attachment of Spacer Arm Molecules

A plurality of spacer arm molecules 60 are attached to an outer surface 56 of a micro-electrode 58, a portion of which is shown in FIG. 7. Spacer molecules 60 can include a polyoxymethylene functional group as a backbone. Each spacer arm molecule 60 can be attached to outer surface 56 by a sulfur atom, for example, as in FIGS. 5A–5C above, or by any other chemically appropriate reactive group. Each spacer arm molecule 60 preferably has an appropriate oxidizable group 62 at the end which is not attached to outer surface 56. If oxidizable group 62 is present, it is preferably oxidized after attachment of spacer arm molecules 60 to outer surface 56. Alternatively and preferably, a different derivatization of spacer arm molecules 60 can be performed so that the end which is not attached to outer surface 56 of micro-electrode 58 is available for reaction with binding entity, as described in Step 3b.

Step 3b: Attachment of Binding Entity

Once spacer arm molecule 60 has an appropriate reactive moiety available, a binding entity 64 is contacted with spacer arm molecule 60. Binding entity 64 should have an appropriate reactive moiety for reacting with at least one functional group of spacer arm molecule 60 and for enabling a covalent bond to form between binding entity 64 and spacer arm molecule 60. In this example, the covalent bond formed between spacer arm molecule 60 and binding entity 64 is an oxime or hydrazone bond, as shown in FIG. 7.

In order to form this bond, spacer arm molecule 60 has a reactive carbonyl group 66 which reacts with an $NH_2$ group of binding entity 64. Binding entity 64 has a general formula $H_2N$—$X_1$—Y—ODN, in which $X_1$ is oxygen or an NH group and Y is a hydrocarbon chain which can be saturated or unsaturated, substituted or unsubstituted. However, binding entity 64 could have substantially any appropriate terminal hydroxyl amine or hydrazine functional group for reacting with spacer arm molecule 60. ODN represents an appropriate oligodeoxynucleotide for the purposes of this example, although substantially any type of binding entity could be substituted.

This second procedure for attaching binding entities 64 to the surface of micro-electrode 58 has a number of advantages. First, similarly to the first procedure, it enables the formation of a two-dimensional hydrogen bond array between the various spacer arm molecules 60. As noted previously, such an array stabilizes the monolayer of binding entities 64 and causes them to be oriented in a particularly desirable position for hybridization with a complementary probe. Second, unlike the first procedure, many different modifications of spacer arm molecule 60 can be made, and different functions added, without exposing binding entity 64 to these chemical reactions. Thus, this second procedure offers great flexibility in preparing spacer arm molecules 60, and ultimately in constructing the monolayer of binding entities itself.

As noted in Step 3(b) above, spacer arm molecule 60 is attached to binding entity 64 by a covalent bond formed during an irreversible chemical ligation process. This ligation process occurs in aqueous media under conditions of pH, buffering compounds and salt concentrations which are compatible with binding entity 64, in this case an oligodeoxynucleotide. Further specific examples of spacer arm molecules 60 are given in FIGS. 8 and 9. All of these molecules include α-silylated ethers or dithianes which are oxidizable in mixed organic-aqueous media, as well as the thiols or sulfides for gold chemisorption which were described previously.

Figure 8:
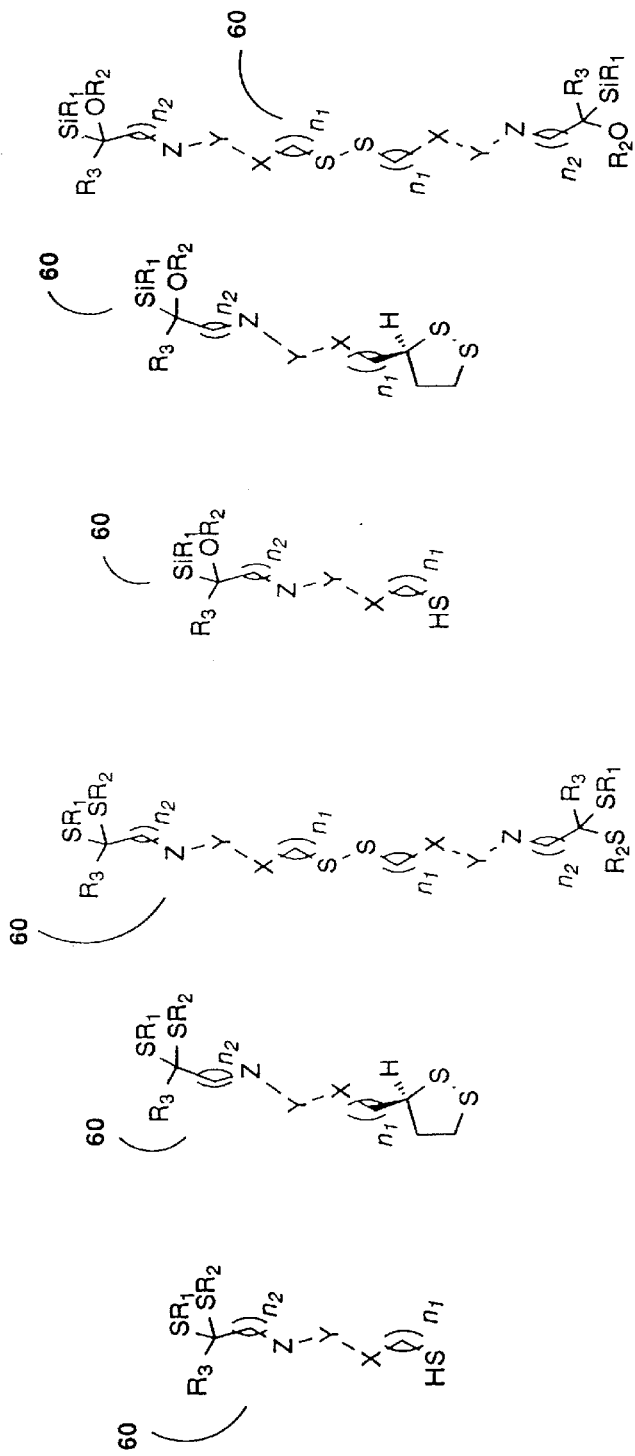
FIGS. 8 and 9 illustrate examples of spacer molecules for attachment to gold micro-electrodes according to the present invention.

FIG. 8 shows six separate examples of spacer arm molecules 60 which include amide or urethane groups within the backbone of the molecule. These molecules are intended only to illustrate the general concept of inclusion of amide or urethane groups in the backbone. Such groups are particularly advantageous for the formation of two-dimensional closely packed hydrogen-bond arrays for increased stability of the monolayer of binding entities, and are thus preferably included as part of the spacer arm molecule.

With regard to the specific examples shown in FIG. 8, the group X—Y—Z is preferably selected from one of the following formulas: $CH_2$—CO—NH, NH—CO—$CH_2$ or NH—CO—NH. $R_1$, $R_2$ and $R_3$ are alkyl or aryl groups, which may be identical or different. An unsaturated hydrocarbon chain of variable length is represented by (>) or (>) $n_1$ or $n_2$, wherein $n_1$ and $n_2$ may be of substantially any suitable number, depending upon the desired length of the spacer molecule.

Figure 9:
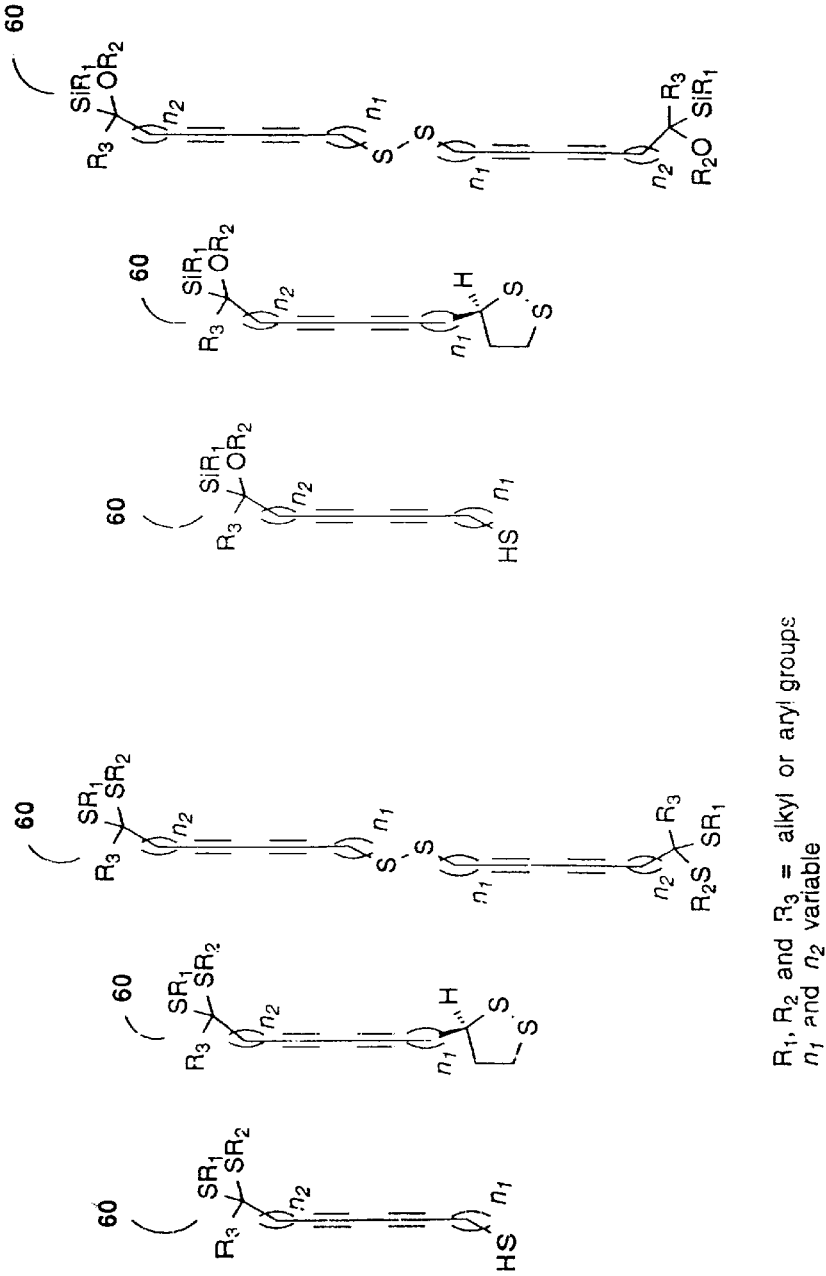

Alternatively, instead of including amide or urethane groups in the backbone of the spacer molecule, (1,3)-diyne groups can be used in their place, or optionally in addition to these groups. FIG. 9 shows six separate examples of spacer molecules 60 which include a (1,3)-diyne group instead of the amide or urethane groups of the molecules of FIG. 8. Other definitions of groups within the formulas are as for FIG. 8.

Figure 10:
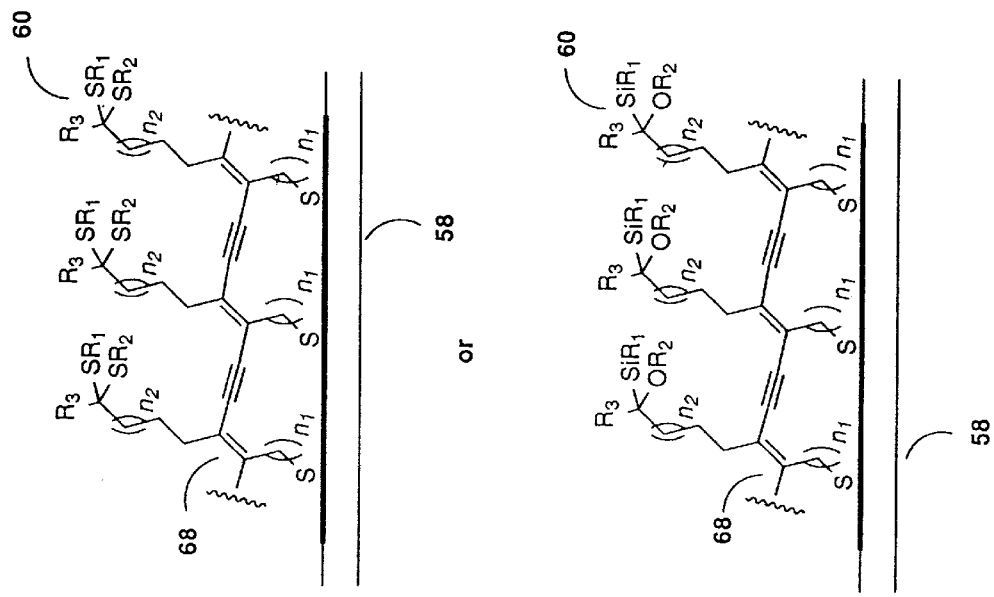
FIG. 10 shows the spacer molecules of FIG. 9 forming a conductive film on the surface of the gold micro-electrodes.

The advantage of including (1,3)-diyne groups in the backbone of the spacer molecule is that they can be polymerized by exposure to ultra-violet (UV) radiation, preferably at 254 nm. Such polymerization is shown in FIG. 10 for two different examples of spacer molecules 60 attached to the surface of micro-electrode 58. After polymerization, a conductive polymerized film 68 is formed on the surface of micro-electrode 58, which has excellent chemical stability especially for non-classical conditions for hybridizing complementary oligodeoxynucleotide probes to oligodeoxynucleotide binding entities. Thus, oligodeoxynucleotide binding entities attached to these spacer molecules would be held both stably and in a desirable orientation for hybridization to a complementary probe.

Such polymerization could optionally be performed on substantially all micro-electrodes simultaneously, preferably after the thiol or disulfide moiety of the spacer molecule had reacted with the gold surface of the micro-electrode but preferably before the oxidizable group of the spacer molecule had been oxidized. The subsequent steps of oxidation of the group which reacts with the binding entity (or a specific group on the binding entity), as well as attachment of the binding entity to the spacer molecule by a chemical reaction forming a covalent bond, could be substantially similar or even identical to those steps described previously. Indeed, such steps could even be performed more efficiently due to the increased stability of the complex formed between the spacer molecule and the surface of the micro-electrode.

Of course, such a functional group as the (1,3)-diyne moieties shown above are exemplary prototypes of the types of functional groups which could be added to the hydrocarbon backbone of the spacer molecule in order to promote the stability and correct orientation of binding entities within the monolayer attached to the micro-electrode surface. Generally, such functional groups preferably can form either non-covalent bonds or covalent bonds with each other in order to achieve these characteristics. Examples of groups which form non-covalent bonds are given in FIG. 8, while examples of groups which form covalent bonds are given in FIG. 9. In either case, these groups enable the spacer molecules to actively form an ordered array of binding entities, rather than merely passively holding these entities a certain distance from the surface of the micro-electrode. Thus, these functional groups within the backbone of the spacer molecule add significant stability and order to the monolayer of binding entities on the surface of the micro-electrode.

Figure 11:
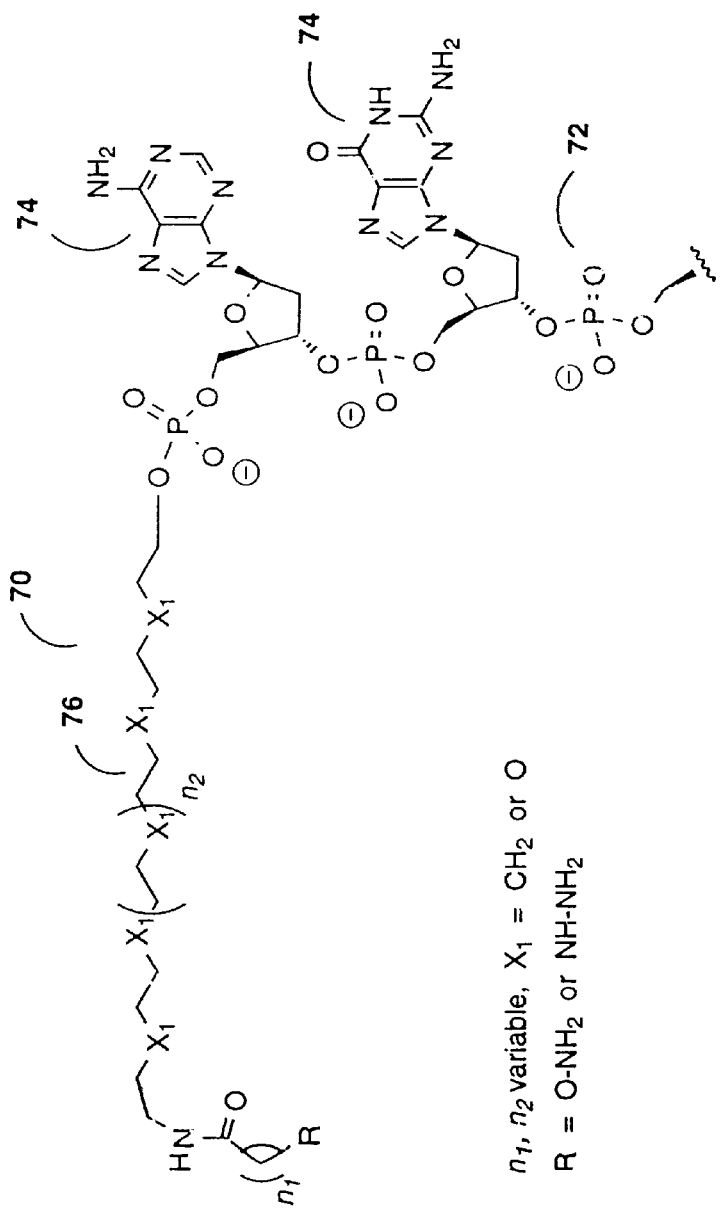
FIG. 11 illustrates a binding entity suitable for use with the spacer molecules of FIGS. 8–10.

Examples of suitably modified oligodeoxynucleotide binding entities for use with the spacer molecules of FIGS. 8 and 9 are shown in FIG. 11. As noted previously, the binding entity preferably must have either a hydroxylamine or hydrazine group in order to react with the carbonyl group of the spacer molecule and form either a oxime or hydrazone bond. Of course, other functional groups could be used in place of the hydroxylamine or hydrazine group, but these are preferred both for the chemical stability of the resultant covalent bond and the general compatibility of the required chemical reaction conditions with oligodeoxynucleotide binding entities themselves.

FIG. 11 shows a modified oligodeoxynucleotide 70 with a structure of type C, which includes a hydroxylamine or hydrazine group. A portion of modified oligodeoxynucleotide 70 is shown, including a core oligodeoxynucleotide 72. Core oligodeoxynucleotide 72 can be of substantially any length, although only two bases 74 are shown. The hydroxylamine or hydrazine group is shown as "R" having the general formula of O—$NH_2$ or NH—$NH_2$, attached to one end of a polymethylene spacer 76. Polymethylene spacer 76 has the general formula $[(CH_2)_2X]_{n2}$—NH—C(=O)—$(CH_2)_{n1}$—R, in which $n_1$ and $n_2$ are variable, X is either $CH_2$ or O, and R is as defined previously.

Polymethylene spacer 76 is shown at the 5' position of core oligodeoxynucleotide 72, although it could also have been added at the 3' end of core oligodeoxynucleotide 72. Modified oligodeoxynucleotides 70 of type C are thus able to become covalently bound to spacer molecules 76 described previously.

EXAMPLE 3

Indium Tin Oxide Micro-electrodes

The preceding two examples, although generally applicable to micro-electrodes constructed of many different materials, were particularly drawn to gold micro-electrodes for the purposes of illustration. However, such micro-electrodes could alternatively be constructed from indium tin oxide, set onto a substrate of glass for support. Arrays of such indium tin oxide micro-electrodes could ultimately be used in a similar fashion as the arrays of gold micro-electrodes described above.

Different methods of attaching the binding entities to the surface of indium tin oxide micro-electrodes, however. Such methods would follow the general outline of the procedure described in Example 2 above, although the specific chemistry of the spacer molecules would change. Briefly, spacer molecules with a silylated functional group would react with the indium tin oxide to form a covalent bond, in a similar manner as the sulfated functional group of the spacer molecules of Example 2 would react with the surface of a gold micro-electrode. Next, a binding entity such as a modified oligodeoxynucleotide would react with the spacer molecule to form a covalent bond. The modified oligodeoxynucleotide could be substantially similar, or even identical, to those described in Example 2 above. Thus, the only change required to the method of Example 2 would be in the chemistry of the initial reaction between the spacer molecule and the surface of the indium tin oxide micro-electrode.

Figure 12:
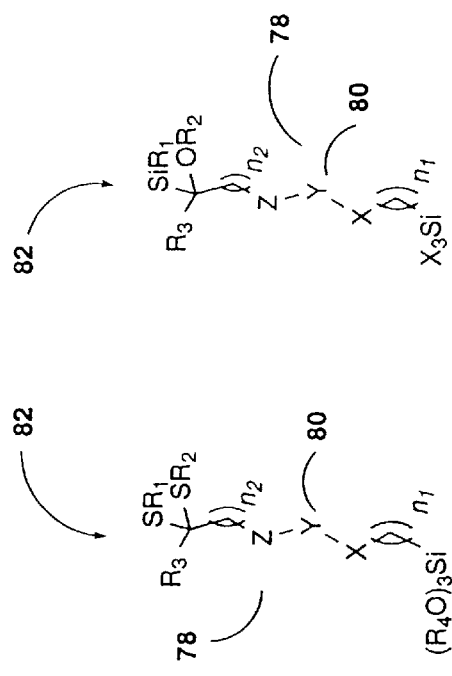
FIGS. 12 and 13 illustrate spacer molecules for attachment to indium tin oxide micro-electrodes according to the present invention.
Figure 13:
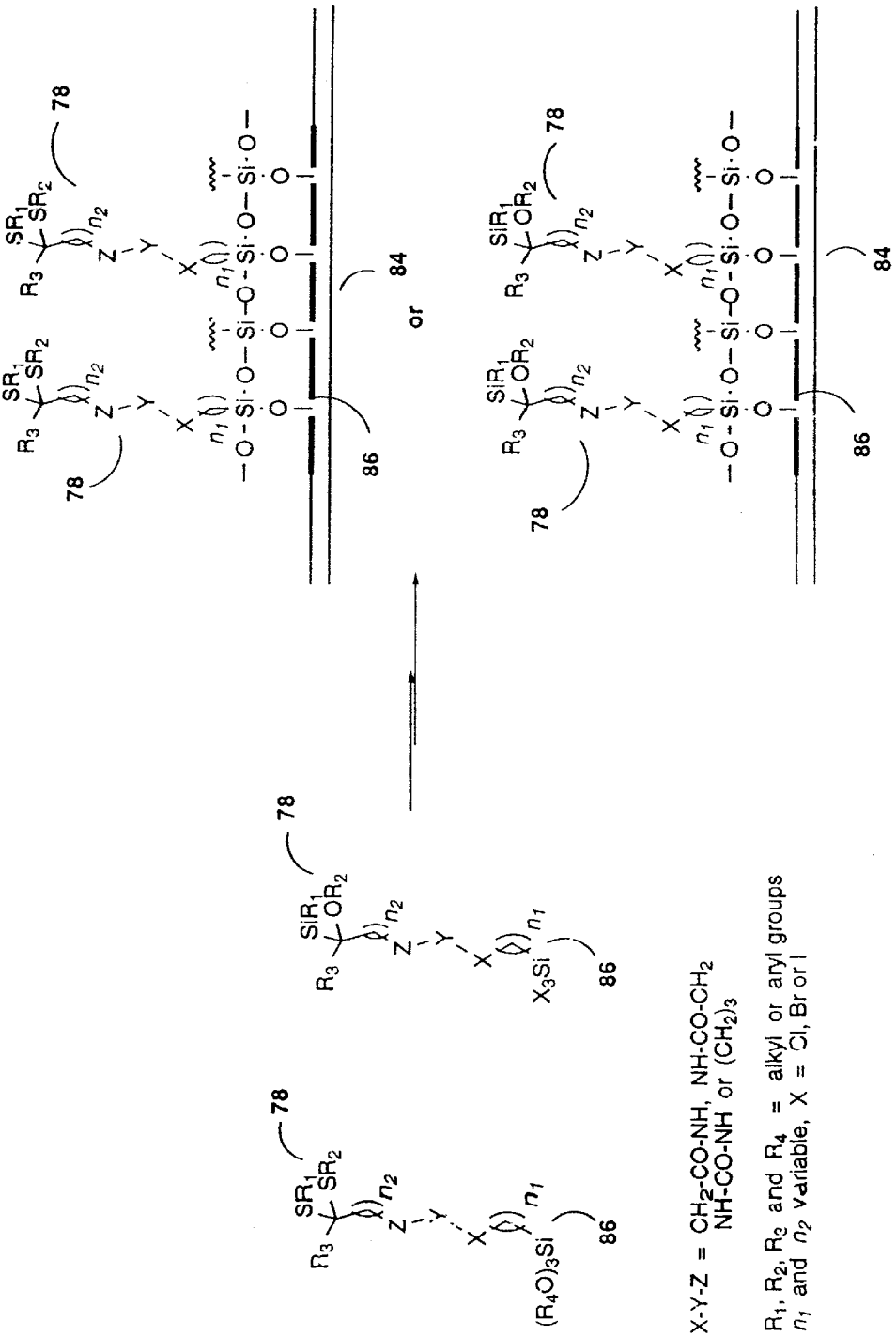

Examples of appropriate spacer molecules are shown in FIG. 12. A spacer molecule 78 is an α-silylated ether or dithiane, including a backbone 80 with amide or urethane groups. The silylated functional group could have the general formula $(R_4O)_3Si$, in which $R_4$ is an alkyl or an aryl group. Alternatively, the silylated functional group could have the general formula $X_3Si$, in which X is chlorine, bromine or iodine. This silylated functional group reacts with oxygen in the indium tin oxide to form a covalent bond between spacer molecule 78 and the micro-electrode, as shown in FIG. 13 below.

Spacer molecule 78 also includes amide or urethane groups in backbone 80, having the general formula X—Y—Z, in which Y is CO, and X and Z are selected from the group consisting of $CH_2$ and NH. Preferably, X—Y—Z has a formula selected from the group consisting of $CH_2$—CO—NH, NH—CO—$CH_2$ and NH—CO—NH.

Also, (>) or (<)$n_1$ or $n_2$ represent methyl groups in backbone 80 of spacer molecule 78, in which $n_1$ and $n_2$ can be any suitable number, depending upon the desired overall length of spacer molecule 78. Finally, spacer molecule 78 has an oxidizable functional group 82, which can be of the general formula

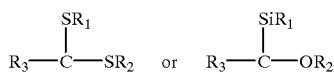

in which $R_1$, $R_2$ and $R_3$ are independently selected from alkyl or aryl groups. Oxidizable functional group 82 can react with a functional group on a binding entity, such as those described in Example 2, to form a covalent bond and thus attach the binding entity to spacer molecule 78.

FIG. 13 shows the chemical reaction in which a silylated functional group 86 of spacer molecule 78 binds to an indium tin oxide micro-electrode 84, a portion of which is shown. Silylated functional group 86 first forms a covalent bond with oxygen from the indium tin oxide of micro-electrode 84. Next, preferably silylated functional groups 86 are polymerized in an oxidation reaction. Such polymerization is shown in FIG. 13 for two different examples of spacer molecules 78 attached to the surface of micro-electrode 84. After polymerization, a conductive polymerized film is formed on the surface of micro-electrode 84, which has excellent chemical stability especially for non-classical conditions for hybridizing complementary oligodeoxynucleotide probes to oligodeoxynucleotide binding entities. Thus, oligodeoxynucleotide binding entities attached to these spacer molecules would be held both stably and in a desirable orientation for hybridization to a complementary probe.

Such polymerization could optionally be performed on substantially all micro-electrodes simultaneously, preferably after the silylated functional group of the spacer molecule had reacted with the indium tin oxide surface of the micro-electrode but preferably before the oxidizable group of the spacer molecule had been oxidized. The subsequent steps of oxidation of the group which reacts with the binding entity (or a specific group on the binding entity), as well as attachment of the binding entity to the spacer molecule by a chemical reaction forming a covalent bond, could be substantially similar or even identical to those steps described previously in Example 2 for gold micro-electrodes. Indeed, such steps could even be performed more efficiently due to the increased stability of the complex formed between the spacer molecule and the surface of the micro-electrode.

Detection System for the Micro-circuit of the Present Invention

This section describes an example of a system for performing a bimolecular interaction between a probe entity and the binding entity attached to the micro-electrodes of the micro-circuit of the present invention, it being understood that this is simply one possible example of using the micro-circuit. For the sake of clarity, the type of bimolecular interaction described will be limited to the interaction, or hybridization reaction, between an oligodeoxynucleotide bound to the micro-electrode surface and a complementary oligodeoxynucleotide probe, it being understood that this is for descriptive purposes only and is not meant to be limiting in any way. The first two examples in this section describe micro-circuit readers for indium tin oxide micro-electrode arrays. The next example describes such a reader for gold micro-electrode arrays. The final example is of a micro-circuit reader suitable for micro-electrode arrays of substantially any material.

Preferably, the presence of the bound complementary oligodeoxynucleotide probe is determined by the detection of a fluorescent moiety which is attached to the complementary probe. A detection system which uses fluorescence as a marker is particularly suitable because it is extremely sensitive. Fluorescence emission can be collected and passed through a series of optical filters to a sensitive detector, such as a photomultiplier tube. By simply scanning the laser or translating the test cell, a two-dimensional fluorescence image of the pattern of binding of complementary probe molecules can be generated in minutes or less. An additional advantage of fluorescence is that multiple colors can be used to label different types of complementary probes.

EXAMPLE 1

Figure 14:
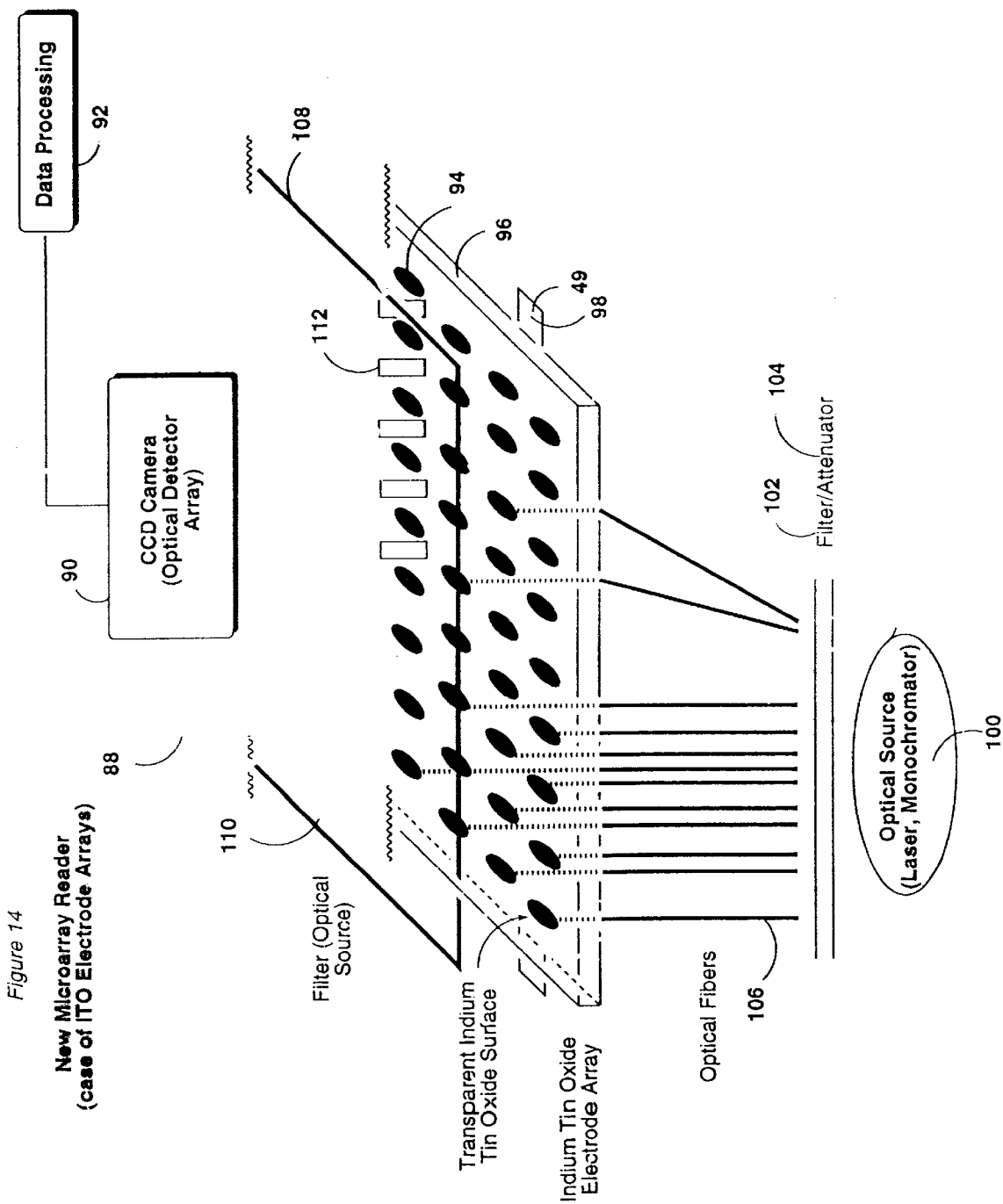
FIG. 14 shows a micro-circuit reader suitable for use with an array of indium tin oxide micro-electrodes according to the present invention.

FIG. 14 shows an exemplary micro-circuit reader suitable for arrays of indium tin oxide micro-electrodes. A micro-circuit reader 88 includes a CCD (charge-coupled device) camera 90. CCD camera 90 has an array of pixels. When light hits a portion of the array, an electrical current is generated by that portion of the array which is then sent to a data processing unit 92 for analysis. Preferably, data processing unit 92 includes a microcomputer (not shown).

The light detected is a fluorescent emission from complementary probe molecules bound to oligodeoxynucleotides which are attached to the surface of a plurality of indium tin oxide micro-electrodes 94. Indium tin oxide micro-electrodes 94 are arranged in an array on a glass support 96, a portion of which is shown for clarity. Preferably, glass support 96 is itself being supported by a plurality of guides 98. It should be noted that both glass support 96 and indium tin oxide micro-electrodes 94 are substantially transparent. Hereinafter, the term "transparent" is defined as permitting passage of lightwaves of at least one wavelength.

Transparency is necessary to enable light from an optical source 100 to pass through glass support 96 and indium tin oxide micro-electrodes 94, and thence to excite fluorescent moieties attached to complementary probes on the surface of micro-electrodes 94. Optical source 100 is selected depending upon the type of fluorescent moiety chosen, but could be a mercury arc lamp, Xenon lamp, a laser or a monochromator, for example. If optical source 100 is a mercury arc lamp or a Xenon lamp, preferably a filter 102 is used to filter light being produced by the lamp, most preferably only passing light of the wavelength or wavelengths which excite the desired fluorescent moiety. Preferably, an attenuator 104 is included, regardless of the type of optical source 100, but after filter 102 if one is present, to reduce the quantity of light reaching micro-circuit 88. Also preferably, light from optical source 100 is transmitted through optical fibers 106 to micro-circuit 88.

Once the excitatory light reaches indium tin oxide micro-electrodes 94, the fluorescent moiety or moieties which are excited by light of that particular wavelength or wavelengths then emit light in a fluorescent emission. Preferably, the emitted light is passed through at least one optical filter 110 before being detected by CCD camera 90. Also preferably, a separator plate 108 is positioned above array of micro-electrodes 94. Separator plate 108 has a plurality of apertures 112, each of which is positioned above one micro-electrode 94. Separator plate 108 acts to confine radiation from each micro-electrode 94 to one portion of CCD camera 90, so that emitted light from fluorescent moieties on one micro-electrode 94 cannot leak and contaminate data collected from a different micro-electrode 94.

EXAMPLE 2

In this Example, the micro-circuit reader includes a multi-anode photomultiplier tube for collecting the light emitted from the fluorescent moieties. An example of such a photomultiplier is obtainable from Hamamatsu Photonics (Tokyo, Japan). The multi-anode photomultiplier tube includes fine mesh diodes which are positioned a few millimeters apart, preferably at similar intervals to the distance between different micro-electrodes in the micro-circuit. High electric fields across the mesh dynodes accelerate electrons away from the photocathode while interference between the channels is minimized by negatively charged mask electrodes. The multi-anode photomultiplier tube has the advantage of operating at high sensitivity and low noise levels while still allowing parallel channel operation. In the case of low photon counts, any interference between emissions from different micro-electrodes will be eliminated during data analysis.

An additional advantage of using such a wide spectral response photomultiplier tube is that the spectrum of detectable light includes both ultra-violet and visible light, and even infra-red radiation if necessary.

Figure 15:
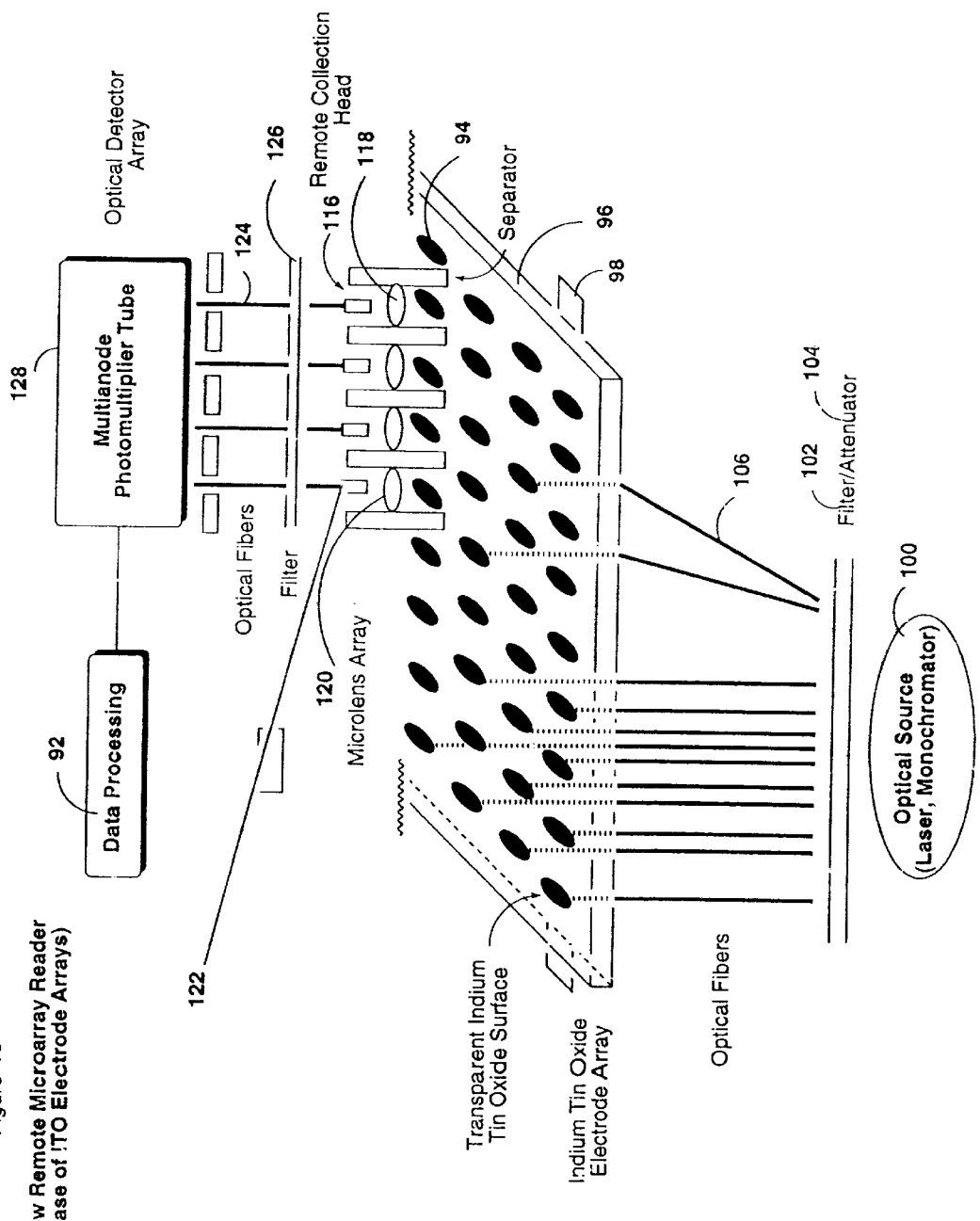
FIG. 15 shows an alternative embodiment of the micro-circuit reader of FIG. 14.

FIG. 15 shows a different exemplary embodiment of a micro-circuit reader 114 for an array of indium tin oxide micro-electrodes 94, including the multi-anode photomultiplier tube. Features which are substantially similar or identical to those shown in FIG. 14 are given the same boldface identification numbers.

In this embodiment, a remote collection head 116 is positioned above micro-electrode array 94. Collection head 116 includes a plurality of apertures 118, one positioned above each micro-electrode 94 in the array. Each aperture 118 includes a converging lens 120 which focuses emitted light from fluorescent moieties at each micro-electrode 94 onto an optical fiber endface 122. Optical fiber endface 122 then transmits the collected light to a support member 124. Preferably, an optical filter 126 is located between endface 122 and support member 124. Support member 124 then passes the collected light to the photocathode of a photomultiplier 128. Processing and analysis of the data is substantially similar to that described in FIG. 14.

EXAMPLE 3

The previous two Examples were concerned with micro-readers suitable for a substantially transparent micro-circuit, such as an array of indium tin oxide micro-electrodes. However, the micro-circuit of the present invention can also include an array of gold micro-electrodes which are not transparent. Such an array requires a different system for the detection of light emitted from the fluorescent moieties on the complementary probes.

Figure 16:
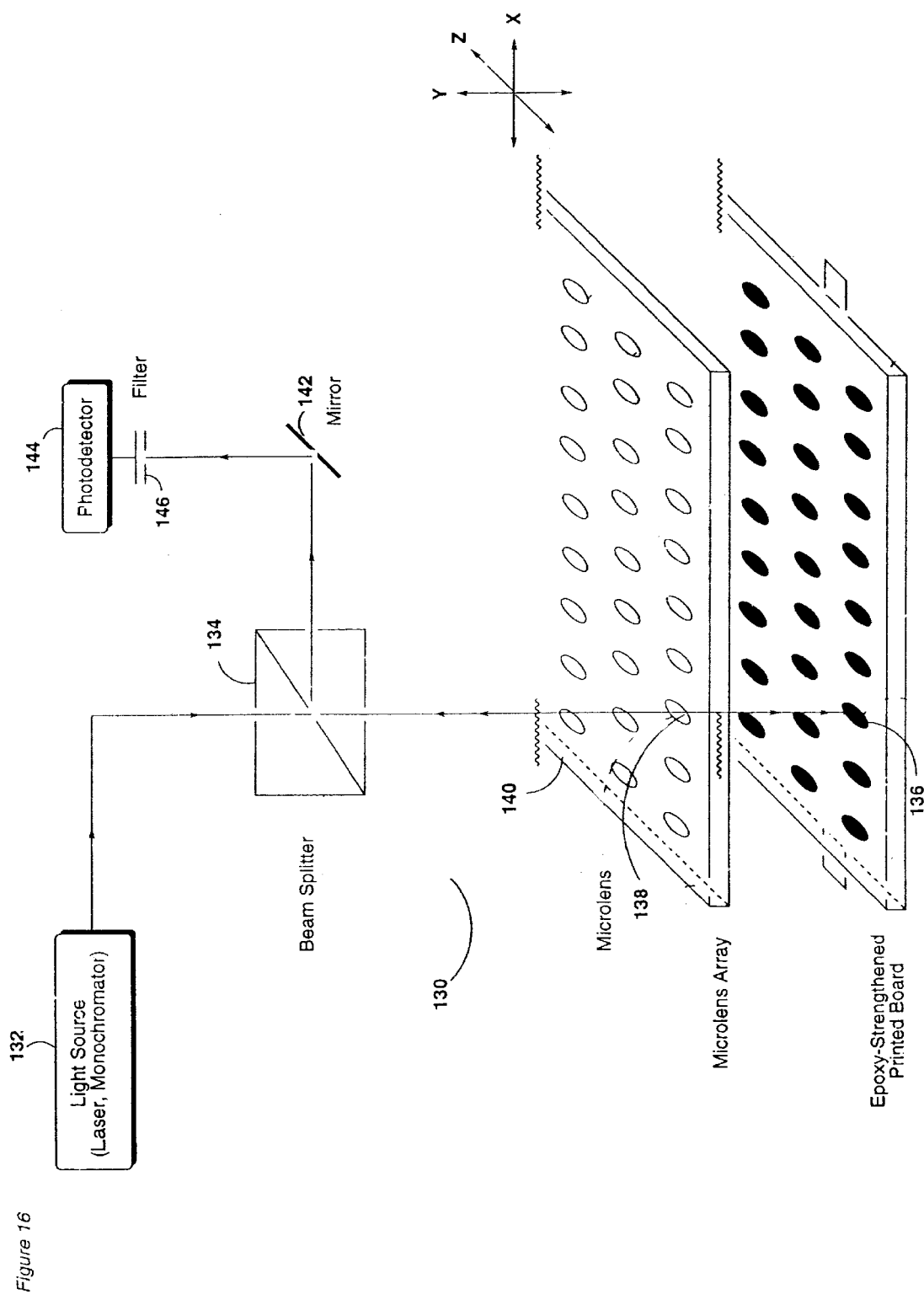
FIG. 16 shows a micro-circuit reader suitable for use with an array of gold micro-electrodes according to the present invention.

One exemplary embodiment of a micro-reader suitable for an array of micro-electrodes is shown in FIG. 16. A micro-reader 130 includes a light source 132 of any suitable type including, but not limited to, a laser, a monochromator, a mercury arc lamp or a Xenon lamp. If a mercury arc lamp or a Xenon lamp is used, a suitable filter is preferably used (not shown). Light passes from light source 132 through a beam splitter 134 and is then focused onto a single micro-electrode 136 by a micro-lens 138, which is part of a micro-lens array 140 as shown. As light from light source 132 hits the surface of micro-electrode 136, any fluorescent moieties present at the surface of micro-electrode 136 are then excited and emit light. The emitted light is then collected by micro-lens 138. Preferably, micro-electrode 136 is substantially concave in shape in order to increase the efficiency of light collection.

After being collected by micro-lens 138, the emitted light is then reflected by beam splitter 134 onto a mirror 142. Mirror 142 reflects the emitted light to a photodetector 144. Preferably, an optical filter 146 filters the emitted light before it is passed to photodetector 144. The processing of the resultant data is similar to that shown for Examples 1 and 2 above.

EXAMPLE 4

Figure 17:
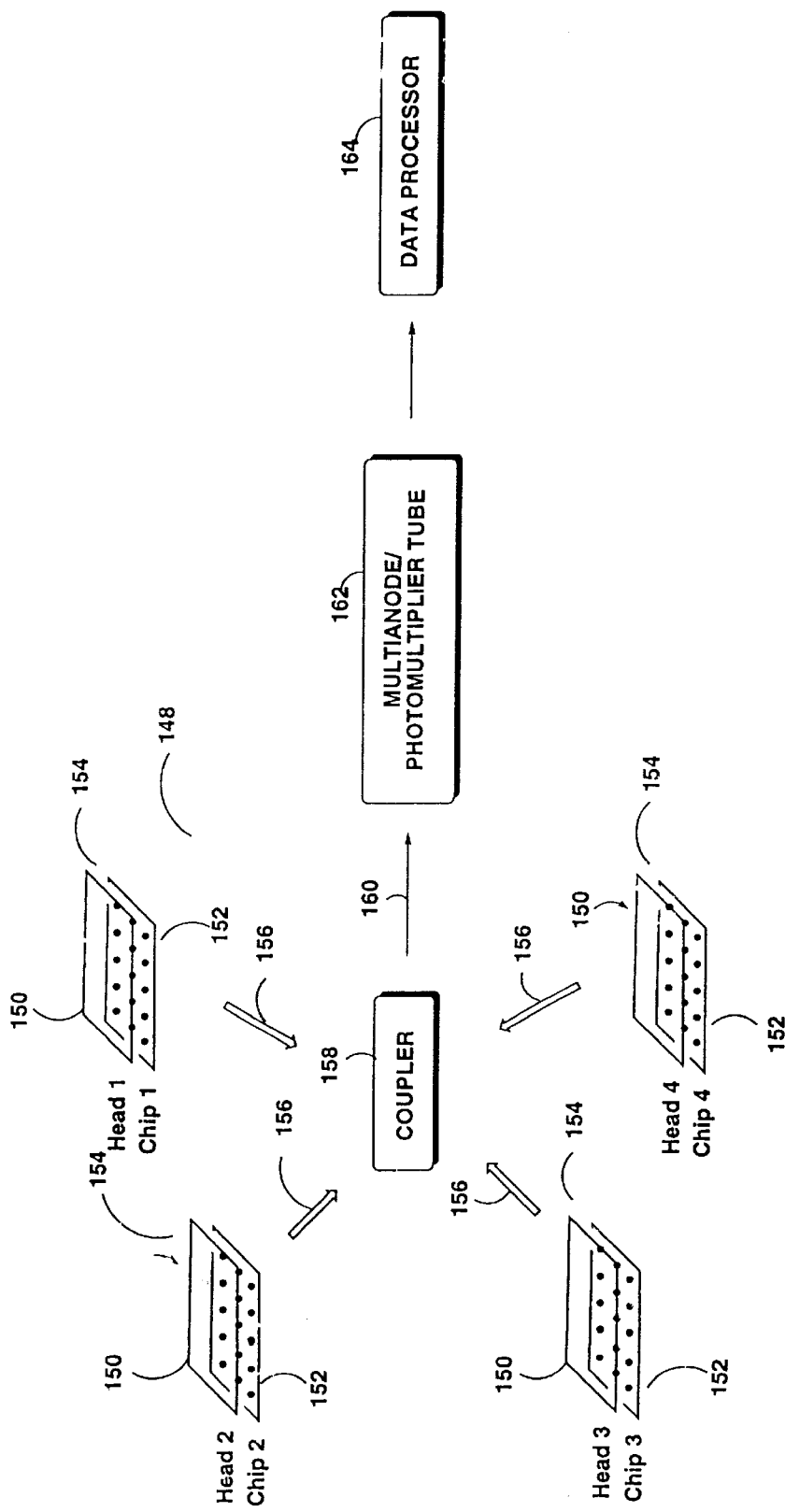
FIG. 17 shows a multiplex micro-circuit reader suitable for use with a plurality of micro-circuits according to the present invention.

Examples 1–3 showed micro-readers which could read a single micro-circuit at a time. However, it is often desirable to be able to read a plurality of micro-circuits relatively rapidly. Furthermore, it would be desirable to be able to read a micro-circuit regardless of the type of micro-electrode employed. FIG. 17 shows an exemplary illustration of a multiplexed micro-circuit reader which can both collect data from a plurality of micro-circuits and which is not limited to substantially transparent arrays of micro-electrodes.

A multiplexed micro-circuit reader 148 includes a plurality of collection heads 150 (four are shown), similar to the collection head shown in FIG. 16. Each collection head 150 is positioned above a separate micro-circuit 152. Each micro-circuit 152 is supported by a separate plate supporting assembly 154.

Each collection head 150 is connected by a respective set of input optical fibers 156 to an optical coupler 158. Optical coupler 158 has a single set of output optical fibers 160 to which each set of input optical fibers 156 is connected. Output optical fibers 160 are then connected to photomultiplier tube 162, which is preferably of the multi-anode type. Data from photomultiplier tube 162 is then passed to a data processing unit 164 for analysis, as for Examples 1–3.

In operation, shutters (not shown) are inserted between all micro-circuits 152 and optical fibers 156, except for one micro-circuit/optical fiber pair. These shutters prevent emitted light from reaching coupler 158, so that only emitted light from one micro-circuit 152 is passed from coupler 158 to photomultiplier tube 162. The shutters can be inserted and removed in sequence, so that emitted light from each micro-circuit 152 is sequentially detected by photomultiplier tube 162. Thus, one set of photodetector electronics could be used for multiple micro-circuits 152 in rapid sequence.

Optionally and preferably, each micro-circuit supporting assembly 154 could include a different type of light source and/or a different optical filter (not shown), enabling multiple types of fluorescent moieties to be used with a single micro-reader system.

Applications of the Microcircuit of the Present Invention

A number of different embodiments of the micro-circuit of the present invention have been described in the preceding sections. This section will describe a number of exemplary applications of the micro-circuit, it being understood that these are only illustrative and are not meant to be limiting in any way. These applications include a variety of multi-step and multiplex reactions, syntheses and analyses, depending upon the binding entities attached to the micro-electrodes of the micro-circuit of the present invention. The present invention provides a number of improvements over traditional methods of performing these reactions, syntheses and analyses. For example, reactants and analytes tend to become concentrated in the relatively small area of the surface of the micro-electrode, thereby increasing the rate of the reaction.

Furthermore, the micro-circuits of the present invention offer a tremendous improvement over prior art devices in that the cycle of protection and deprotection of the micro-electrodes significantly increases the specificity of binding of particular binding entities. Finally, the micro-circuits of the present invention can also preferably include monolayers of binding entities which have been additionally stabilized by the presence of covalent or non-covalent bonds. These bonds serve to both enhance the chemical stability of the monolayer, and to ensure that the binding entities are kept in the proper orientation for interaction with any other additional molecule, such as a complementary probe. Thus, the present invention represents a significant improvement over the prior art for these applications.

Examples of applications which are suitable for the micro-circuits of the present invention include, but are not limited to, hybridizations of DNA and RNA oligonucleotides; molecular biology reaction procedures such as restriction enzyme reactions and analysis, ligase reactions, kinasing reactions and amplification procedures; antibody/antigen reactions; various diagnostic assays such as hybridization analysis, gene analysis, fingerprinting and immunodiagnostics; bimolecular conjugation procedures such as the covalent and non-covalent labeling of nucleic acids, enzymes, proteins or antibodies with suitable functional groups, or with reporter moieties such as fluorophores; biopolymer synthesis procedures such as the combinatorial synthesis of oligonucleotides or peptides; synthetic polymer synthesis such as the synthesis of carbohydrates or linear polyacrylates; ligands to cell receptor/cell; and macromolecular syntheses.

It is particularly contemplated that the micro-circuit of the present invention could be used to perform diagnostic assays for genetic diseases or pathogenic micro-organisms. For example, micro-circuits with specific oligodeoxynucleotide sequences as binding entities could be used to detect the presence of key gene sequences associated with genetic diseases including, but not limited to, Tay-Sachs disease, sickle cell anemia, phenylketonuria, adult polycystic kidney disease and cystic fibrosis in prenatal diagnosis or carrier detection. Furthermore, specific micro-circuits could be prepared to detect and diagnose the presence of such pathogenic microorganisms as viruses, bacteria, fungi or parasites. Such micro-circuits would have sets of ligands based upon either synthetic or natural epitopes which are proteinaceous, polysaccharide, deoxyribonucleic acid, ribonucleic acid or lipidic, and which would react with specific complementary moieties included within or produced by the particular microorganism, or specific antibodies raised against the microorganism. Thus, diagnosis of many different types of diseases could be performed with the device of the present invention.

As an example of an application which can be performed with the device of the present invention, a description is given below of a method for performing a nucleic acid hybridization. Hereinafter, the term "nucleic acid hybridization" refers to a hybridization reaction occurring between any natural or synthetic forms and derivatives of nucleic acids including, but not limited to, deoxyribonucleic acid (DNA), ribonucleic acid (RNA), polynucleotides and oligonucleotides. A description of a method for performing an antibody-antigen reaction is given below in a subsequent section. Hereinafter, the term "antibody" refers to any molecule which is capable of specifically binding to a particular ligand, hereinafter referred to as the "antigen". Although antibodies and antigens are both typically proteins or peptides, or a fragment thereof, as used herein these terms refer to any molecule which is capable of behaving as an "antibody" or "antigen", including both synthetic molecules and biomolecules.

Antibody-antigen reactions and nucleic acid hybridizations are two of the most important diagnostic reactions currently performed between two biomolecules. They are also two of the most difficult reactions to perform both accurately yet sensitively, since false negative results and high background noise are common problems. Thus, it is difficult to design assays which are suitable for clinical use outside of a research laboratory setting with conventional diagnostic tools, a problem which is solved by the method and device of the present invention.

EXAMPLE 1

Nucleic Acid Hybridization

The method described herein is intended as an illustration of a nucleic acid hybridization and is not meant to be limiting in any way. For the purposes of description, the nucleic acids discussed herein are oligodeoxynucleotides or fragments of DNA, it being understood that other types of nucleic acids or nucleic acid chains could be used in place of oligodeoxynucleotides.

As a first step in the hybridization procedure, a micro-circuit is prepared as described previously. Briefly, different target DNA fragments are preferably attached to each individual micro-electrode, although a plurality of micro-electrodes could have DNA fragments of identical nucleotide sequence attached if desired. The attachment process can either be a one-step process, in which a functional group on the DNA fragment reacts directly with the surface of the micro-electrode, or a two step process. In the two-step process, a spacer molecule is attached to the surface of the micro-electrode first. Next, the DNA fragment is attached to the spacer molecule. In any case, preferably the micro-electrodes are first all protected together, and are then individually deprotected as needed in order to perform the attachment of the DNA fragment. This cycle of protection and deprotection confers a high degree of specificity on the attachment process.

Once the micro-circuit has been prepared with the desired target DNA fragment or fragments, a labeled complementary probe is then allowed to interact with the target DNA fragment or fragments. The term "complementary probe" as used herein refers to a nucleic acid chain with a complementary sequence, such as a DNA fragment, which can uniquely bind specifically to a target DNA fragment having a particular nucleic acid sequence. The complementary probe is labeled with a reporter group, such as a fluorophore or a radioactive substance, which can then be detected by a suitable detection device. Preferably, the reporter group is a fluorophore and emitted light is detected according to one of the schemes described previously.

In order to prevent mismatched probes from binding to the target DNA fragment and thereby give misleading results, the stringency of hybridization must be appropriately adjusted. The term "stringency" refers to the conditions in which the hybridization occurs, such as temperature, salt concentration and pH. Conditions which tend to promote binding of two DNA fragments regardless of specificity, such as low temperature, are said to have low stringency. Unfortunately, certain combinations of target and probe DNA fragments will only bind specifically under low stringency conditions, while other such combinations must be hybridized under conditions of high stringency in order to prevent mismatches from occurring. Thus, often hybridization conditions must be adjusted depending upon the sequences of the target and probe DNA fragments.

Such adjustments can be calculated theoretically, so that the necessity for high or low stringency conditions can be determined without the need for empirical experimentation. One advantage of the micro-circuit of the present invention is that each micro-electrode is preferably individually electronically activatable. By activating a micro-electrode at a particular level of power, less stable mismatched target-probe DNA fragment pairs can be denatured, leaving only those probe fragments specifically bound to target DNA fragments. Such electronic stringency is described in more detail in U.S. Pat. No. 5,605,662.

Alternatively, more conventional methods of adjusting the stringency of hybridization can be employed. For example, temperature or salt concentrations can be adjusted, in place of, or in addition to, the electronic stringency method described previously. Thus, the device of the present invention offers an opportunity to improve conventional hybridization methods.

EXAMPLE 2

Antibody-antigen Reactions

Reactions between antibodies and antigens are both easier and more difficult to perform than the nucleic acid hybridizations described previously. First, both antibodies and antigens are typically abundant in biological samples, such as blood, milk, saliva, mucous, urine, cerebrospinal fluid or other tissues. Such abundance reduces the difficulty of detection often seen with samples of genetic material such as DNA from a patient. However, since antibodies and antigens are often both proteins or protein fragments, the specificity of interaction, and the reaction conditions required to obtain the greatest such specificity, are much less clear. With target and probe DNA fragments, it is immediately obvious if the resultant bound complex will be specific or mismatched simply by examining the sequence of each fragment. The rules of interaction between two protein epitopes are not known to such a high degree, so that determining proper reaction conditions is potentially more difficult.

However, the micro-circuit of the present invention has at least one advantage over traditional assay media for antibody-antigen reactions, such as ELISA's or Western blots. If proper spacer molecules are chosen, such as the previously described thiolipid molecules, the resultant binding entity monolayer could have some of the properties of a lipid biomembrane. Such properties could potentially stabilize a target proteinaceous binding entity, as well as maintain the binding entity in a proper orientation for interaction with a proteinaceous probe. Thus, the device of the present invention could increase both sensitivity and accuracy of antibody-antigen reaction assays.

As a first step in the assay, a micro-circuit is prepared with a proteinaceous binding entity. For the sake of clarity, this binding entity will hereinafter be referred to as the antigen. Different specific antigens are preferably attached to each individual micro-electrode, although alternatively a plurality of micro-electrodes could have identical antigens attached. The process of attachment could either be one-step or two-step, as described for DNA fragments previously. One particular advantage for attaching antigens is that the number of amino acid residues, as well as the backbone peptidic bonds themselves, are available for derivatization. For example, the amino acid residue cysteine has a reactive thiol group which can be used in a chemical reaction to attach a spacer molecule. Thus, antigens can be relatively easily attached to the surface of a micro-electrode by using well known chemical cross-linking reagents as spacer molecules.

Once the antigen has been attached, the micro-circuit can be incubated with the desired antibody in a buffered salt solution, such as those used for ELISA immunoreactions or even Western blots, according to methods which are well known in the art. Optionally, additional washing steps can be performed with the buffered solution to remove any non-specifically bound antibody. Finally, the micro-circuit can be analyzed with a micro-reader as described previously, selected is according to the type of reporter molecule which is attached to the antibody. The use of fluorophores as reporter molecules for antibodies is well known in the art, and a suitable fluorophore could easily be selected by one of ordinary skill in the art.

It will be appreciated that the above descriptions are intended only to serve as examples, and that many other embodiments are possible within the spirit and the scope of the present invention.

What is claimed is:

1. A micro-circuit system comprising:
   (a) a support;
   (b) a power source;
   (c) a plurality of micro-electrodes attached to said support, each of said plurality of micro-electrodes being separately selectively electronically activatable by said power source;
   (d) a metallic protective layer attached to said at least one micro-electrode, said protective layer being removed upon electronic activation of each micro-electrode by said power source, such that said metallic protective layer is removed from at least one micro-electrode; and
   (e) a binding entity for attachment to said at least one micro-electrode with said metallic protective layer removed, such that said binding entity only attaches to each electrode when said metallic protective layer has been removed.

2. The micro-circuit of claim 1, wherein said at least one micro-electrode comprises a material selected from the group consisting of gold, aluminum, silver, tin, copper, platinum, palladium, semiconductor materials and indium tin oxide.

3. The micro-circuit of claim 1, wherein said support comprises a material selected from the group consisting of silicon, silicon dioxide, plastic, ceramic and glass.

4. The micro-circuit of claim 1, wherein said power source is a direct current source.

5. The micro-circuit of claim 1, wherein said metallic protective layer is constructed from copper.

6. The micro-circuit of claim 5, wherein said copper is attached to said micro-electrode by a process selected from the group consisting of electrodeposition, electroless plating and vapor deposition.

7. The micro-circuit of claim 1, further comprising an orientation layer, said orientation layer being attached to said protective layer.

8. The micro-circuit of claim 7, wherein said orientation layer comprises molecules formed from a material selected from the group consisting of thiolipid and terminally silylated lipid, wherein a sulfur group of said thiolipid is attached to said protective layer or a silicon group of said terminally silyated lipid is attached to said protective layer.

9. The micro-circuit of claim 8, wherein a structure of said molecules comprises a hydrocarbon backbone substituted with at least one functional moiety selected from the group consisting of (1,3)-diyne, amide and urethane.

10. The micro-circuit of claim 9, wherein said functional moiety of said hydrocarbon backbone is capable of polymerization, such that a covalent bond is formed between at least two of said molecules.

11. The micro-circuit of claim 9, wherein said functional moiety of said hydrocarbon backbone is capable of forming a hydrogen bond, such that a non-covalent bond is formed between at least two of said molecules.

12. The micro-circuit of claim 8, wherein said molecules are polyoxymethylene substituted with a functional moiety selected from the group consisting of sulfur, disulfide, silicon, and silicon dioxide.

13. The micro-circuit of claim 1, further comprising a reservoir for holding liquid buffer such that said buffer is able to contact said at least one micro-electrode.

14. An system comprising:
   (a) a micro-circuit comprising:
      (i) a support;
      (ii) a power source;
      (iii) a plurality of micro-electrodes attached to said support, each of said plurality of micro-electrodes being separately selectively electronically activatable by said power source;
      (iv) a metallic protective layer attached to said at least one micro-electrode, said protective layer being removed upon electronic activation of each micro-electrode by said power source, such that said metallic protective layer is removed from at least one micro-electrode; and
      (v) a binding entity for attachment to said at least one micro-electrode with said metallic protective layer removed, such that said binding entity only binds to each electrode when said metallic protective layer has been removed; and
   (b) a micro-circuit reader for reading said micro-circuit.

15. The system of claim 14, wherein said micro-circuit reader comprises a light source for producing light and a detector for detecting emitted light.

16. The system of claim 15, wherein said light source is selected from the group consisting of Xenon lamp, laser and monochromator.

17. The system of claim 15, wherein said detector is selected from the group consisting of photomultiplier tube, charge-coupled device camera and multianode photomultiplier tube.

18. The system of claim 15, wherein said micro-circuit reader further comprises a microlens, said microlens focusing said light produced by said light source substantially on said micro-electrode, and said microlens focusing said emitted light on said detector.

19. The system of claim 15, wherein said micro-circuit reader further comprises a beam splitter, said beam splitter permitting said light produced by said light source to reach said micro-electrode, and said beam splitter reflecting said emitted light at an angle such that said emitted light is detectable by said detector.

20. The system of claim 14, wherein said plurality of micro-electrodes includes at least a first micro-electrode and at least a second micro-electrode with said metallic protective layer being removed, said at least a first micro-electrode having a second binding entity attached thereto, and said at least a second micro-electrode having a second binding entity attached thereto, wherein said first binding entity is different from said second binding entity.

21. The system of claim 1, wherein said plurality of micro-electrodes includes at least a first micro-electrode and at least a second micro-electrode with said metallic protective layer being removed, said at least a first micro-electrode having a second binding entity attached thereto, and said at least a second micro-electrode having a second binding entity attached thereto, wherein said first binding entity is different from said second binding entity.

* * * * *